(12) United States Patent
Lee

(10) Patent No.: US 9,925,398 B2
(45) Date of Patent: Mar. 27, 2018

(54) ANGIOGENIC PEPTIDE

(75) Inventor: Taehoon Lee, Pohang (KR)

(73) Assignee: NOVACELL TECHNOLOGY INC., Pohang (KR)

( * ) Notice: Subject to any disclaimer, the term of this patent is extended or adjusted under 35 U.S.C. 154(b) by 641 days.

(21) Appl. No.: 12/989,065

(22) PCT Filed: Apr. 23, 2009

(86) PCT No.: PCT/KR2009/002136
§ 371 (c)(1),
(2), (4) Date: Oct. 21, 2010

(87) PCT Pub. No.: WO2009/131395
PCT Pub. Date: Oct. 29, 2009

(65) Prior Publication Data
US 2011/0110875 A1    May 12, 2011

Related U.S. Application Data

(60) Provisional application No. 61/047,338, filed on Apr. 23, 2008.

(51) Int. Cl.
| | |
|---|---|
| *A61K 38/08* | (2006.01) |
| *C07K 7/06* | (2006.01) |
| *C07K 5/083* | (2006.01) |
| *A61P 17/02* | (2006.01) |
| *A61K 8/64* | (2006.01) |
| *A61Q 19/02* | (2006.01) |
| *A61Q 19/08* | (2006.01) |
| *A61Q 19/00* | (2006.01) |
| *A61K 38/00* | (2006.01) |

(52) U.S. Cl.
CPC ........... *A61Q 19/08* (2013.01); *A61K 8/64* (2013.01); *A61Q 19/02* (2013.01); *C07K 7/06* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 5,885,782 A | * | 3/1999 | Edwards | A01N 37/46 435/7.1 |
| 6,559,126 B2 | | 5/2003 | Tournaire et al. | |
| 7,223,835 B2 | | 5/2007 | Selwood et al. | |
| 7,504,111 B2 | * | 3/2009 | Fontana et al. | 424/249.1 |
| 2004/0006780 A1 | | 1/2004 | Gerber et al. | |
| 2005/0019826 A1 | | 1/2005 | Tournaire et al. | |
| 2005/0260581 A1 | * | 11/2005 | Fontana et al. | 435/6 |

FOREIGN PATENT DOCUMENTS

| | | | |
|---|---|---|---|
| DE | 10 2004 055 54 | | 2/2006 |
| FR | 2 706 300 | | 12/1994 |
| WO | WO 98/57174 | * | 6/1988 |
| WO | 98/26793 | | 6/1998 |

OTHER PUBLICATIONS

Aramburu, J. et al., "Affinity-Driven Peptide Selection of an NFAT Inhibitor More Selective Than Cyclosporin A", Science, vol. 285, pp. 2129-2133 (1999).
Bae, Yoe-Sik et al., "Identification of novel chemoattactant peptides for human leukocytes", Blood, vol. 97, No. 9, pp. 2854-2861 (2001).
Berridge, M., "Inositol trisphosphate and calcium signalling", Nature, vol. 361, pp. 315-325 (1993).
Bussolino, F. et al., "Molecular mechanisms of blood vessel formation", TIBS, 22: pp. 251-256 (1997).
Faehling, Martin et al., "Essential role of calcium in vasular endothelial growth factor A-induced signaling: mechanism of the antiangiogenic effect of carboxyamidotraiazole", The FASEB Journal, 16 (2002).
Folkman, J., "Angiogenesis in cancer, vascular, rheumatoid and other disease", Nature Medicine, vol. 1, No. 1, pp. 27-30 (1995).
Guidoboni, Massimo et al., "Retinoic Acid Inhibits the Proliferative Response Induced by CD40 Activation and Interleukin-4 in Mantle Cell Lymphoma", Cancer Research, 65:(2), pp. 587-595 (2005).
Hayashi, Shinichiro et al., "Synthetic Hexa- and Heptapeptides That Inhibit IL-8 from Binding to and Activating Human Blood Neutrophils", Journal of Immunology, 154: pp. 814-821 (1995).
Houghten, Richard A. et al., "Generation and use of synthetic peptide combinatorial libraries and basic research and drug discovery", Nature, vol. 354, pp. 84-86 (1991).
Kiselyov, Kirill et al., "Signalling specificity in GPCR-dependent $Ca^{2+}$ signalling", Cellular Signalling, 15: pp. 243-253 (2003).
Kohn, Elise C. et al, "Angiogenesis: Role of calcium-mediated signal transduction", Proc. Natl. Acad. Sci. USA, vol. 92, pp. 1307-1311 (1995).
Risau, W., "Mechanisms of angiogenesis", Nature, vol. 386, pp. 671-674 (1997).
Database Geneseq, Dec. 28, 2007, "Oryza sativa amino acid sequence SEQ ID No. 144352." XP002643584.
Database Geneseq, Nov. 7, 2001, "Human immune/haematopoietic antigen SEQ ID No. 15290" XP002643585.
Hardy et al, "Angiogenesis induced by novel peptides selected from a phage display library by screening human vascular endothelial cells under different physiological conditions" Peptides, Elsevier, Amsterdam, vol. 28, No. 3, Feb. 7, 2007, pp. 691-701, XP005877278.

(Continued)

Primary Examiner — James H Alstrum-Acevedo
Assistant Examiner — Tara L Martinez
(74) Attorney, Agent, or Firm — Lex IP Meister, PLLC

(57) ABSTRACT

The present application discloses angiogenic peptides that cause intracellular calcium release in target cells and thereby induce proliferation, migration, and capillary-like tube formation in primary cultured endothelial cells. The angiogenic peptides can be used for preventing and/or treating angiogenesis-related conditions, especially wound healing, treating foot and leg ulcers in a subject, etc. In addition, the angiogenic peptides can be used for cosmetics a constituent of cosmetics for aged skin, for examples, anti-wrinkle and skin whitening.

4 Claims, 14 Drawing Sheets

(56) References Cited

OTHER PUBLICATIONS

Lee C H et al, "Identification of novel synthetic peptide showing angiogenic activity in human endlthelial cells", Peptides, Evol. 30, No. 2, Feb. 1, 2009, pp. 409-418, XP025873868.
Sun-Ju Lee et al: "Antioxidant and Anti-Melanogenic Effect of the Novel Synthetic Hexapeptide (SFKLRY-NH2)", International Journal of peptide research and therapeutics; formerly known as letters in peptide science, kluwer academic publishers, vol. 15, No. 4, Sep. 23, 2009, pp. 281-289, XP019751683.
Roselyne Binetruy-Rournaire et al., "Identification of a peptide blocking vascular endothelial growth factor (VEGF)-mediated antiogenesis" In the EMBO Journal vol. 19 No. 7, pp. 1525-1533, 2000.
Daria A. Narmoneva et al., "Self-assembling short oligopeptides and the promotion of angiogenesis" In Biomaterials 26 (2005) 4837-4846.

\* cited by examiner

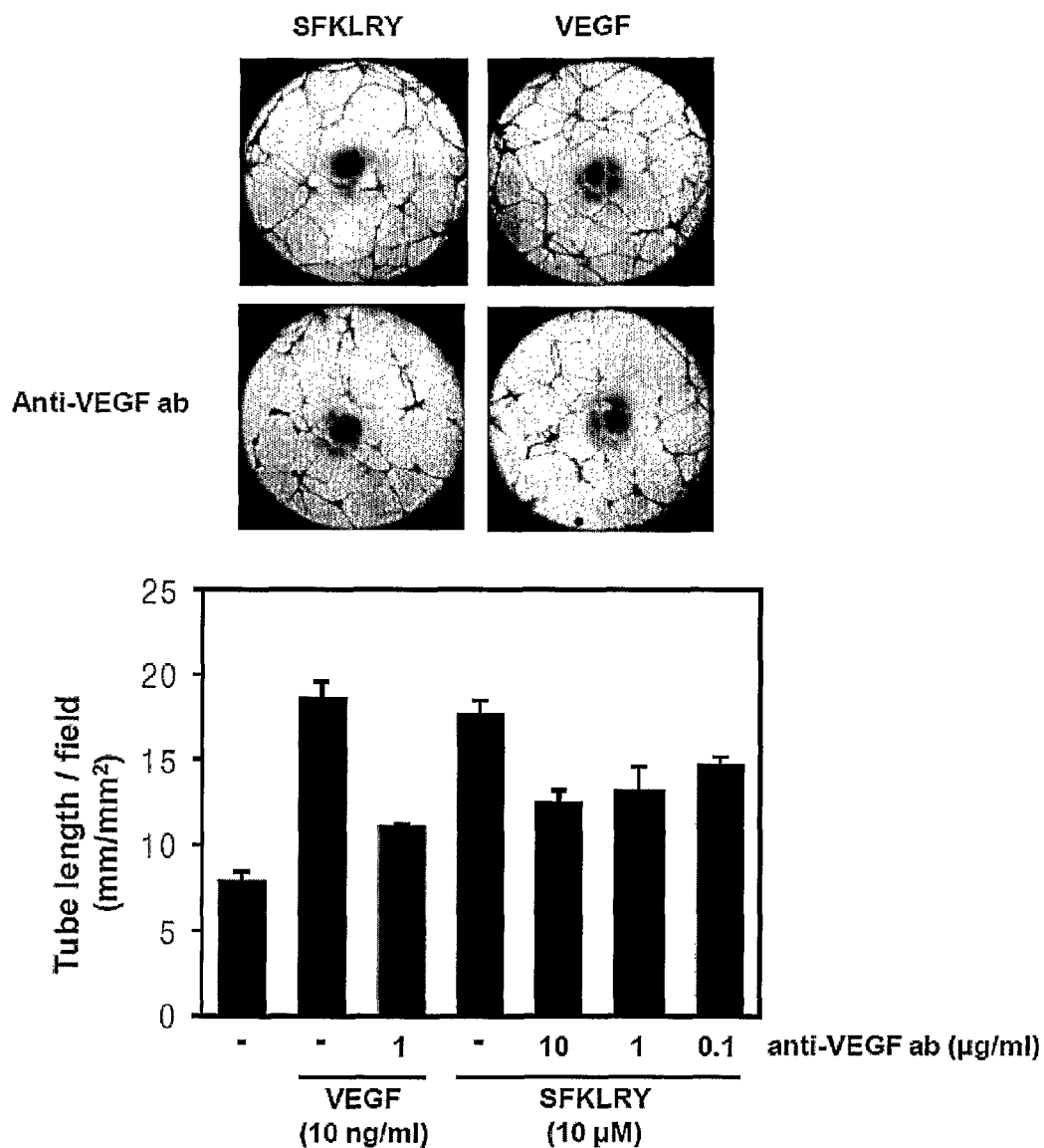

SFKLRY-NH2 [μM]

SFKLRY-NH2 [μM]

SEQUENCE LISTING

<160> NUMBER OF SEQ ID NOS: 28

<210> SEQ ID NO 1
<211> LENGTH: 6
<212> TYPE: PRT
<213> ORGANISM: Artificial Sequence
<220> FEATURE:
<223> OTHER INFORMATION: synthetic peptide

<400> SEQUENCE: 1

Ser Phe Lys Leu Arg Tyr
 1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (6)
<223> OTHER INFORMATION: Amidation

<400> SEQUENCE: 2

Ser Phe Lys Leu Arg Tyr
 1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (6)
<223> OTHER INFORMATION: amidation
<220> FEATURE:
<221> NAME/KEY: VARIANT
<222> LOCATION: (1)
<223> OTHER INFORMATION: Serine in D-form

<400> SEQUENCE: 3

Ser Phe Lys Leu Arg Tyr
 1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (2)
<223> OTHER INFORMATION: Phe in D-form
<220> FEATURE:
<221> NAME/KEY: VARIANT
<222> LOCATION: (6)
<223> OTHER INFORMATION: Amidation

<400> SEQUENCE: 4

Ser Phe Lys Leu Arg Tyr
 1               5

<210> SEQ ID NO 5
<211> LENGTH: 6
<212> TYPE: PRT
<213> ORGANISM: Artificial Sequence

```
<220> FEATURE:
<223> OTHER INFORMATION: Synthetic peptide
<220> FEATURE:
<221> NAME/KEY: VARIANT
<222> LOCATION: (3)
<223> OTHER INFORMATION: Lys in D-form
<220> FEATURE:
<221> NAME/KEY: VARIANT
<222> LOCATION: (6)
<223> OTHER INFORMATION: Amidation

<400> SEQUENCE: 5

Ser Phe Lys Leu Arg Tyr
 1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (6)
<223> OTHER INFORMATION: Amidation
<220> FEATURE:
<221> NAME/KEY: VARIANT
<222> LOCATION: (4)
<223> OTHER INFORMATION: Leu in D-form

<400> SEQUENCE: 6

Ser Phe Lys Leu Arg Tyr
 1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (5)
<223> OTHER INFORMATION: Arg in D-form
<220> FEATURE:
<221> NAME/KEY: VARIANT
<222> LOCATION: (6)
<223> OTHER INFORMATION: Amidation

<400> SEQUENCE: 7

Ser Phe Lys Leu Arg Tyr
 1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (6)
<223> OTHER INFORMATION: Tyr in D-form
<220> FEATURE:
<221> NAME/KEY: VARIANT
<222> LOCATION: (6)
<223> OTHER INFORMATION: Amidation

<400> SEQUENCE: 8

Ser Phe Lys Leu Arg Tyr
 1               5
```

```
<210> SEQ ID NO 9
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (5)
<223> OTHER INFORMATION: Amidation

<400> SEQUENCE: 9

Phe Lys Leu Arg Tyr
 1               5

<210> SEQ ID NO 10
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (4)
<223> OTHER INFORMATION: amidation

<400> SEQUENCE: 10

Lys Leu Arg Tyr
 1

<210> SEQ ID NO 11
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (3)
<223> OTHER INFORMATION: amidation

<400> SEQUENCE: 11

Leu Arg Tyr
 1

<210> SEQ ID NO 12
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (5)
<223> OTHER INFORMATION: amidation

<400> SEQUENCE: 12

Ser Phe Lys Leu Arg
 1               5

<210> SEQ ID NO 13
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (4)
<223> OTHER INFORMATION: Amidation
```

<400> SEQUENCE: 13

Ser Phe Lys Leu
  1

<210> SEQ ID NO 14
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (3)
<223> OTHER INFORMATION: Amidation

<400> SEQUENCE: 14

Ser Phe Lys
  1

<210> SEQ ID NO 15
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (6)
<223> OTHER INFORMATION: Amidation

<400> SEQUENCE: 15

Ser Phe Arg Leu Arg Tyr
  1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (6)
<223> OTHER INFORMATION: Amidation

<400> SEQUENCE: 16

Ser Phe Lys Leu Arg Arg
  1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (6)
<223> OTHER INFORMATION: Amidation

<400> SEQUENCE: 17

Ser Phe Ile Leu Arg Tyr
  1               5

<210> SEQ ID NO 18
<211> LENGTH: 6
<212> TYPE: PRT
<213> ORGANISM: Artificial Sequence

```
<220> FEATURE:
<223> OTHER INFORMATION: Synthetic peptide
<220> FEATURE:
<221> NAME/KEY: VARIANT
<222> LOCATION: (6)
<223> OTHER INFORMATION: Amidation

<400> SEQUENCE: 18

Ser Phe Ile Leu Arg Arg
 1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (6)
<223> OTHER INFORMATION: amidation

<400> SEQUENCE: 19

Ser Phe Lys Leu Arg Trp
 1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (6)
<223> OTHER INFORMATION: Amidation

<400> SEQUENCE: 20

Ser Phe Ile Leu Arg Trp
 1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (6)
<223> OTHER INFORMATION: Amidation

<400> SEQUENCE: 21

Ser Phe Lys Leu Arg Phe
 1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (6)
<223> OTHER INFORMATION: amidation

<400> SEQUENCE: 22

Ser Phe Ile Leu Arg Phe
 1               5
```

<210> SEQ ID NO 23
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (6)
<223> OTHER INFORMATION: Amidation

<400> SEQUENCE: 23

Ser Phe Lys Leu Arg His
 1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (6)
<223> OTHER INFORMATION: Amidation

<400> SEQUENCE: 24

Thr Phe Lys Leu Arg Tyr
 1               5

<210> SEQ ID NO 25
<211> LENGTH: 21
<212> TYPE: DNA
<213> ORGANISM: Artificial Sequence
<220> FEATURE:
<223> OTHER INFORMATION: Forward primer for amplifying human VEGF

<400> SEQUENCE: 25
gaggagggca gaatcatcac g                                        21

<210> SEQ ID NO 26
<211> LENGTH: 21
<212> TYPE: DNA
<213> ORGANISM: Artificial Sequence
<220> FEATURE:
<223> OTHER INFORMATION: Reverse primer for amplifying human VEGF

<400> SEQUENCE: 26
atcgcatgag gggcacacag g                                        21

<210> SEQ ID NO 27
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa is serine or threonine
<220> FEATURE:
<221> NAME/KEY: VARIANT
<222> LOCATION: (3)
<223> OTHER INFORMATION: Xaa is lysine, arginine, or isoleucine
<220> FEATURE:
<221> NAME/KEY: VARIANT
<222> LOCATION: (6)
<223> OTHER INFORMATION: Xaa is phenylalanine, tryptophan, tyrosine,
      arginine, or histidine

```
<400> SEQUENCE: 27

Xaa Phe Xaa Leu Arg Xaa
 1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa is serine or threonine
<220> FEATURE:
<221> NAME/KEY: VARIANT
<222> LOCATION: (3)
<223> OTHER INFORMATION: Xaa is lysine, arginine, or isoleucine
<220> FEATURE:
<221> NAME/KEY: VARIANT
<222> LOCATION: (6)
<223> OTHER INFORMATION: Xaa is tryptophan, tyrosine, arginine, or
      histidine

<400> SEQUENCE: 28

Xaa Phe Xaa Leu Arg Xaa
 1               5
```

ANGIOGENIC PEPTIDE

CROSS-REFERENCE TO RELATED APPLICATIONS

This application is a National Stage under 35 U.S.C. 371 of PCT/KR2009/002136 filed Apr. 23, 2009 which claims priority under 35 U.S.C. § 119(e) from U.S. Provisional application No. 61/047,338 filed Apr. 23, 2008, the disclosures of which are incorporated herein by reference in their entireties for all purposes.

FIELD OF THE INVENTION

The present invention relates to angiogenic peptides that cause intracellular calcium release in target cells and thereby induce proliferation, migration, and capillary-like tube formation in primary cultured endothelial cells. In addition, the angiogenic peptides can be used for preventing and/or treating angiognesis-related conditions, especially wound healing, treating foot and leg ulcers in a subject, etc. In addition, the angiogenic peptides can be used for cosmetics a constituent of cosmetics for aged skin, for examples, anti-wrinkle and skin whitening.

BACKGROUND OF THE INVENTION

Angiogenesis, the growth of new blood vessels from preexisting vasculature, is a fundamental process in a variety of physiological and pathological conditions including wound healing, embryonic development, chronic inflammation, and tumor progression and metastasis (J. Folkman, *Nat. Med.* 1 (1995), pp. 27-31; W. Risau, *Nature* 386 (1997), pp. 671-674). In the course of angiogenesis, complex cellular processes take place, including degradation of extracellular matrix, proliferation, migration, and morphological differentiation of endothelial cells to form tubes. This entire process is orchestrated by local factors that modulate neovascularization (F. Bussolino, et al., *Trends Biochem. Sci.* 22 (1997), pp. 251-256), and changes in the angiogenic balance can mediate the 'angiogenic switch'. Perturbation of the angiogenic switch can cause severe problems in the blood vessels.

Calcium plays a key role in signaling events evoked by various extracellular stimuli and coordinating a large variety of cellular functions (M. J. Berridge, *Nature* 361 (1993), pp. 315-325; K. Kiselyov, et al., *Cell Signal* 15 (2003), pp. 243-253). Increased intracellular $Ca^{2+}$ is indispensable for adhesion, collagenolytic activity, migration, and proliferation of human endothelial cells and capillary outgrowth in vivo (E. C. Kohn, et al., *Proc. Natl. Acad. Sci. USA* 92 (1995), pp. 1307-131). Actually, vascular endothelium growth factor (VEGF), a receptor tyrosine kinase (RTK) ligand, and sphingosine-1-phosphate (S1P), a G-protein-coupled receptor (GPCR) ligand, induce neovascularization by modulating intracellular $Ca^{2+}$ levels (M. Faehling, et al., *FASEB J.* 16 (2002), pp. 1805-1807; M. Guidoboni, et al., *Cancer Res.* 65 (2005), pp. 587-595). Therefore, investigating the $Ca^{2+}$-mobilizing properties in endothelial cells might provide important information for the comprehensive understanding of the physiological processes involved in angiogenesis.

The strategy of positional-scanning of synthetic-peptide combinatorial library (PS-SPCL) has been used to isolate peptides that have angiogenic potential (R. A. Houghten, et al., *Nature* 354 (1991), pp. 84-86). Moreover, the PS-SPCL method has successfully been applied to screen useful peptides that are involved in various biological processes, resulting in the identification of several peptides such as interleukin-8-specific antagonists (S. Hayashi, et al., *J Immunol.* 154 (1995), pp. 814-824), inhibitor for nuclear factor of activated T cells (J. Aramburu, et al, *Science* 285 (1999), pp. 2129-2133), and the immunomodulatory peptides (Y. S. Bae, et al., *Blood* 97 (2001), pp. 2854-2862).

SUMMARY OF THE INVENTION

The screening of synthetic peptide library was carried out to obtain biologically active synthetic peptides act on endothelial cells, and the present inventors have identified a novel peptide that potently induces angiogenic activities in vitro and ex vivo. Furthermore, the present inventors provide evidence that angiogenic activity of SFKLRY-$NH_2$ is mediated by induction of VEGF-A in endothelial cells.

An embodiment of the inventions provides an angiogenic peptide sequence selected in 6 to 15 amino acids long that is active for promoting cell migration, angiogenesis, or collagen synthesis or for inhibition of melanin formation. The angiogenic peptide comprises essential hexa-peptide and a connecting peptide constituting 1 to 9 amino acids. Optionally, the angiogenic peptide is modified by substituting the C-terminal carboxyl group with —$NH_2$. The angiogenic activity of the angiogenic peptide is mediated by up-regulation of vascular endothelial growth factor (VEGF).

Another embodiment of the present invention provides a composition for healing wound, promoting collagen synthesis or inhibiting melanin synthesis, comprising the angiogenic peptide. The composition is a pharmaceutical composition for wound healing comprising the angiogenic peptide as an active ingredient, and a pharmaceutically acceptable carrier. The composition is a cosmetic composition for improving the condition of aged skin comprising the angiogenic peptide as an active ingredient, and a cosmetically acceptable carrier. The cosmetic composition is active composition is active for anti-wrinkle and skin whitening.

Further embodiment provides a method of promoting angiogenesis in a mammal, which the method comprises administering to a subject in need, an effective amount of an angiogenic peptide.

Still further embodiment provides a method of healing wound in a subject comprising the steps of: providing a wound healing effective amount of the angiogenic peptide or a peptide mimic thereof to the subject in need thereof.

In yet another aspect, the invention is directed to a method of improving wrinkle comprising administering an effective amount of the angiogenic peptide or a peptide mimic thereof to a subject in need thereof.

In still another aspect, the invention is directed to a method of attenuating skin pigmentation administering an effective amount of the angiogenic peptide or a peptide mimic thereof to a subject in need thereof.

In another aspect, the invention is directed to a method of identifying anti-angiogenic molecules comprising the steps of: providing an endothelial cell; contacting the cell with a candidate antagonist compound; and identifying the candidate antagonist compound as an antagonist compound, if the candidate inhibits the angiogenic activity of the polypeptide described above or a peptide mimic thereof.

BRIEF DESCRIPTION OF THE DRAWINGS

These and other objects of the invention will be more fully understood from the following description of the invention, the referenced drawings attached hereto and the claims appended hereto.

The present invention will become more fully understood from the detailed description given herein below, and the accompanying drawings which are given by way of illustration only, and thus are not limitative of the present invention, and wherein;

FIGS. 6A-6B show anti-VEGF antibody suppress SFKLRY-NH2 (SEQ ID NO: 2)-induced tube formation in HUVECs. Cells were incubated for 24 h in medium containing SFKLRY-NH2 (SEQ ID NO: 2) (10 μM) or VEGF-A (10 ng/mL) with anti-VEGF-A neutralizing antibody (0.1, 1, or 10 μg/mL). After incubation for 24 h, the tubular-like structures were photographed and the length of tube formation was measured. The data are representative from one of two independent experiments and values are means of the two independent experiments. *P<0.05 compared with vehicle treatment.

DETAILED DESCRIPTION OF THE PREFERRED EMBODIMENTS

Figure 1A:
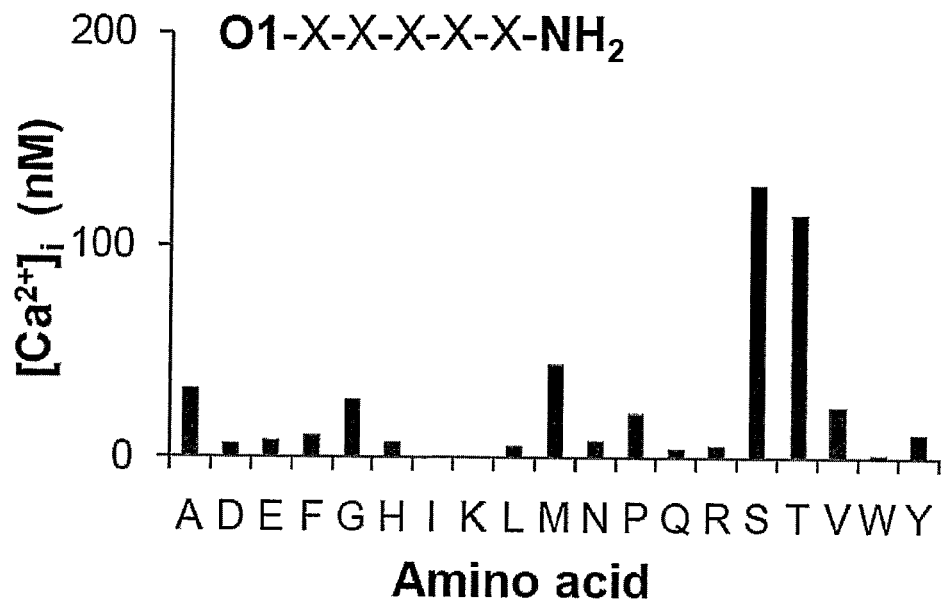
FIG. 1A to 1F show the initial screening of the PS-SPCLs for peptides increasing intracellular calcium in MS-1 cells where each panel indicates the results obtained with the peptide pools with known amino acids at each of the six positions of the hexapeptides. The six positions were individually defined (e.g., O1, O2) by one of the 19 L-amino acids. The remaining five positions consist of mixtures (X) of the 19 L-amino acids (excluding Cystein). The library consists of 114 peptide pools; the PS-SPCL in total is made up of 47,045,881 different peptides. [Ca2+]i increase was measured fluorometrically using Fura-2/AM as described in Materials and Methods. This result represents one of three independent experiments.
Figure 1B:
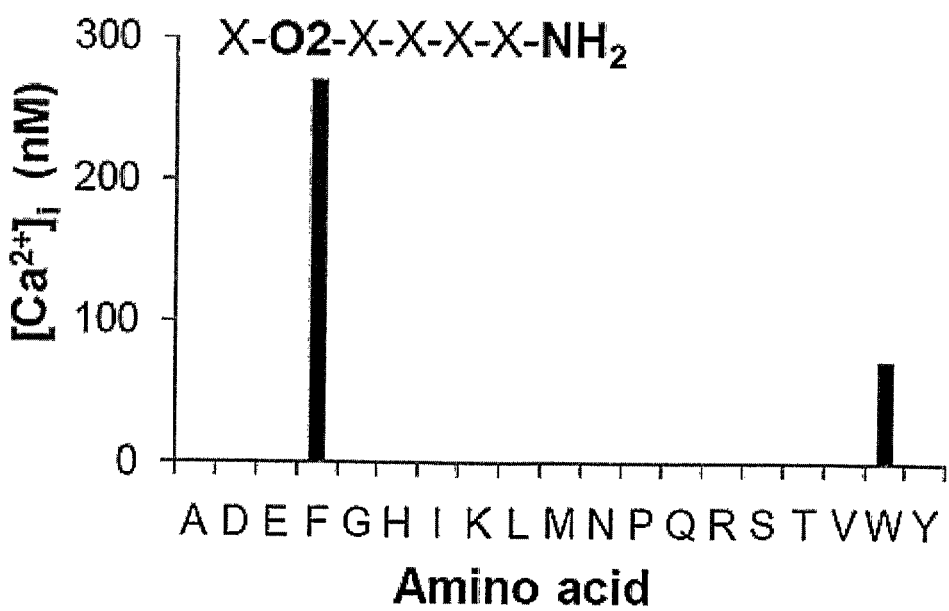
Figure 1C:
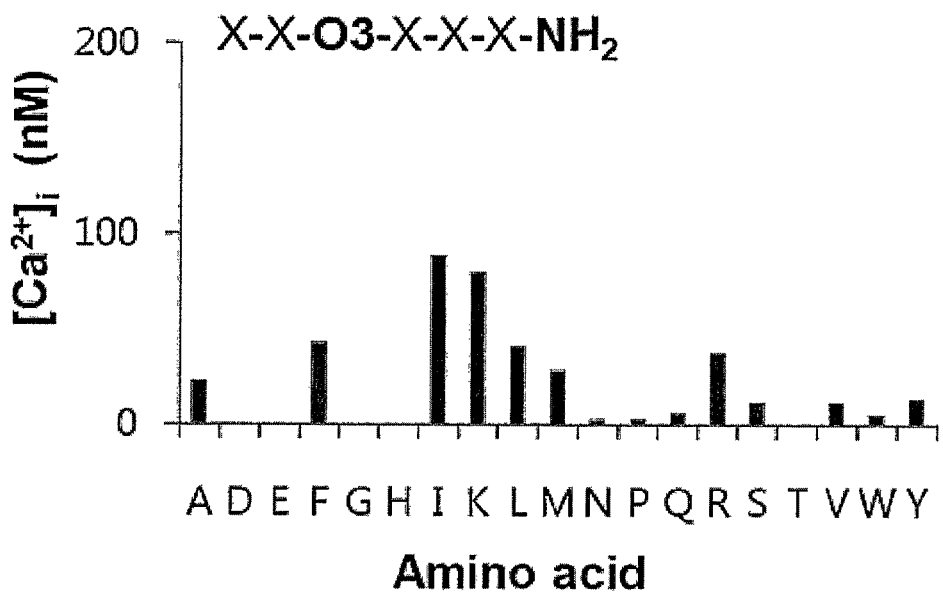
Figure 1D:
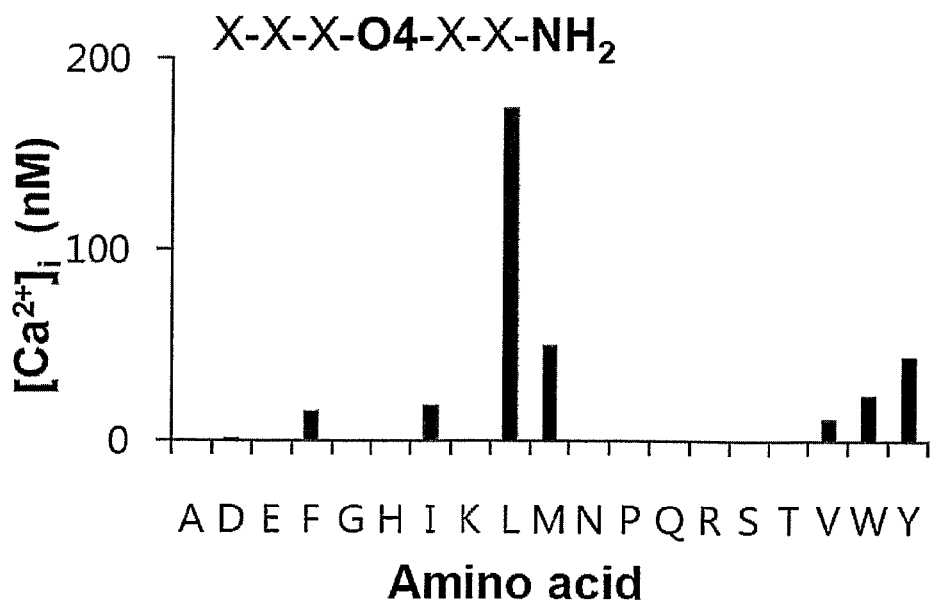
Figure 1E:
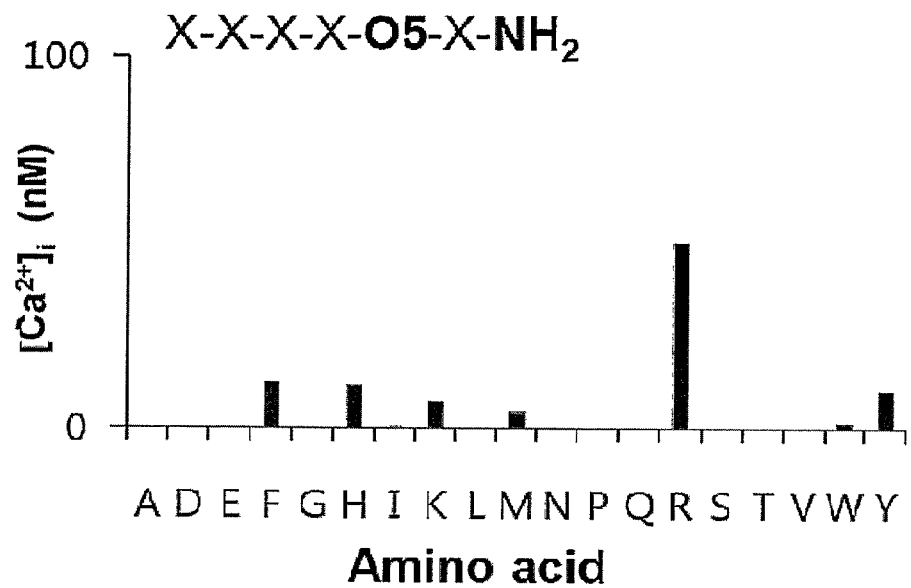
Figure 1F:
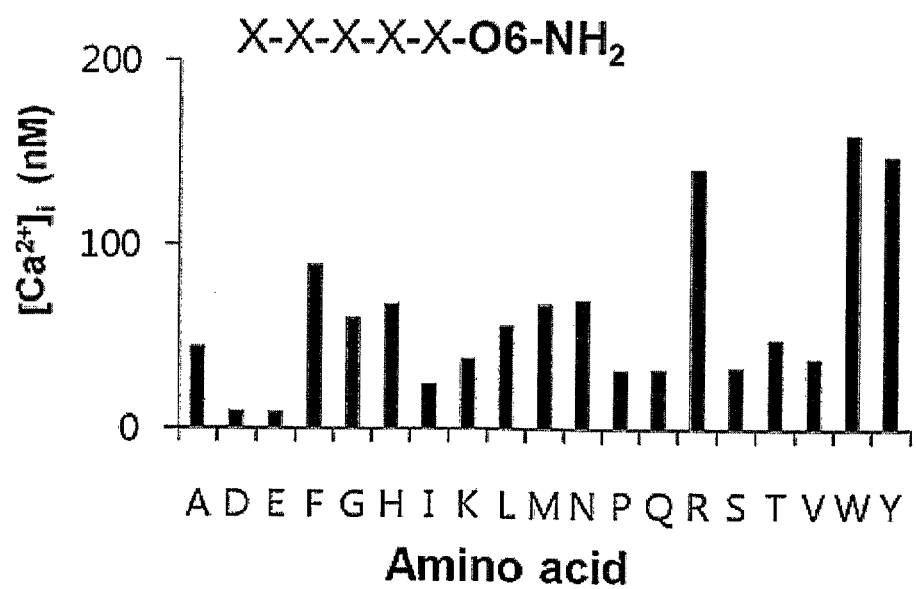

A series of novel peptides inducing [Ca$^{2+}$]$_i$ increase in endothelial cells were disclosed by accommodating positional scanning method of synthetic peptide combinatorial library (PS-SPCL). Among the peptides, SFKLRY-NH$_2$ (SEQ ID NO:2), a prototype peptide was proven to induce DNA synthesis, migration, and tube formation through PTX-sensitive-G protein/PLC-mediated [Ca$^{2+}$]$_i$ increase in endothelial cells, which are the essential steps for angiogenesis. Identification of SFKLRY-NH$_2$ (SEQ ID NO: 2) is noticeable in angiogenesis studies as a small peptide. SFKLRY-NH$_2$ (SEQ ID NO:2) showed angiogenic activity not only in vitro and ex vivo but also had dramatic wound healing activity in rat model. Moreover, the treatment of the peptides stimulated the synthesis of collagen and inhibited the melanin synthesis in skin fibroblasts.

The present invention is directed to a prototype peptide having an amino acid sequence of SEQ ID NO: 2 and a conservative variant or functional fragment thereof. The angiogenic peptide may be from about 6 to 15 amino acids long, from 6 to 10 amino acids long, from 6 to 7 amino acids long or 6 amino acids long, and includes an amino acid sequence of X$_1$FX$_2$LRX$_3$ as an essential part and a peptide constituting 1 to 9 amino acids connected to the C-terminus of X$_1$FX$_2$LRX$_3$. The angiogenic peptide can be modified by substituting the terminal carboxyl group with —NH2. The Examples of the angiogenic peptides includes a peptide consisting of SEQ ID NOs:1, 2, 8, 12, 14, or 15 to 24.

As used herein, the angiogenic peptides refers to an oligopeptide that may be from about 6 to about 15 amino acids long including a hexapeptide having a amino acid sequence of chemical formula I. Further, the peptide is a compound that stimulate $[Ca^{2+}]_i$ increase and thereby induce capillary-like tube formation in endothelial cells.

$X_1FX_2LRX_3$

Wherein, X1 is serine or threonine;

X2 is lysine, arginine, or isoleucine; and

X3 is phenylalanine, tryptophan, tyrosine, arginine, or histidine.

The most active amino acids at each position were: Ser (S) and Thr (T) in the first position; Phe (F) in second; Ile (I), Lys (K), and Arg (R) in third; Leu (L) in fourth; Arg (R) in fifth; and Arg (R), Phe (F), Trp (W), Tyr (Y), and H is (H) in sixth.

As used herein, the term, "angiogenesis" refers to the growth of new blood vessels, or "neovascularization," and involves the growth of new blood vessels of relatively small caliber composed of endothelial cells. Angiogenesis is an integral part of many important biological processes including cancer cell proliferation solid tumor formation, inflammation, wound healing, repair of injured ischemic tissue, myocardial revascularization and remodeling, ovarian follicle maturation, menstrual cycle, and fetal development. New blood vessel formation is required for the development of any new tissue, whether normal or pathological, and thus represents a potential control point in regulating many disease states, as well as a therapeutic opportunity to encourage growth of normal tissue and "normal" angiogenesis.

The complete process for angiogenesis is not entirely understood, but it is known to involve the endothelial cells of the capillaries in the following ways:

(1) The attachment between the endothelial cells and the surrounding extracellular matrix (ECM) is altered, presumably mediated by proteases and glycosidases, which permit the destruction of the basement membrane surrounding the microvascular endothelial cells, thus allowing the endothelial cells to extend cytoplasmic buds in the direction of chemotacetic factors;

(2) There is a "chemotacetic process" of migration of the endothelial cells toward the tissue to be vascularized; and (3) There is a "mitogenesis process" (e.g., proliferation of the endothelial cells to provide additional cells for new vessels). Each of these angiogenic activities can be measured independently utilizing in vitro endothelial cell cultures.

Wounds are internal or external bodily injuries or lesions caused by physical means, such as mechanical, chemical, bacterial, or thermal means, which disrupt the normal continuity of structures. Such bodily injuries include contusions, wounds in which the skin is unbroken, incisions, wounds in which the skin is broken by a cutting instrument, and lacerations, wounds in which the skin is broken by a dull or blunt instrument. Wounds may be caused by accidents or by surgical procedures.

Wound healing consists of a series of processes whereby injured tissue is repaired, specialized tissue is regenerated, and new tissue is reorganized. Wound healing is usually divided into three phases: the inflammatory phase, the proliferative phase, and the remodeling phase. Fibronectin has been reported to be involved in each stage of the wound healing process, particularly by creating a scaffold to which the invading cells can adhere. Initially, many mediators, such as fibronectin and fibrinogen, are released to the wound site. Thereafter, angiogenesis and re-epithelialization take place (U.S. Pat. No. 5,641,483). Repair of injured tissue due to ischemia is a form of wound healing which requires extensive remodeling and re-vascularization. An infarct is, by definition, and area of tissue ischemic necrosis caused by occlusion of local blood circulation. The resulting necrotic lesion leaves the affected tissue deprived of oxygen and nutrients. In the heart, obstruction of coronary circulation in particular, results in myocardial infarction. As the ischemic myocardium undergoes rapid oxygen starvation, the hypoxic microenvironment of the infected cardiac muscle induces the synthesis of angiogenic factors to attempt re-vascularization. For example vascular endothelium growth factor (VEGF) is known to be produced in the areas of the myocardium that have undergone an infarction (Ref).

In one embodiment, the invention is directed to screening for a compound such as a polypeptide, a peptide mimetic, or chemical compound that stimulate $[Ca^{2+}]_i$ increase and thereby induce capillary-like tube formation in endothelial cells. It is expected that the compound will treat persons suffering from diseases evoked by an impaired blood supply, including foot and leg ulcers and retinopathy associated with diabetes or wounds.

Various libraries may be used including phage display library or chemical library to screen for compounds that stimulate $[Ca^{2+}]_i$ increase in endothelial cells. Another approach utilizes two hybrid systems (e.g., yeast or mammalian two-hybrid systems) to identify compounds that induce blood vessel formation in the subject including treating diseases evoked by an impaired blood supply, including foot and leg ulcers and retinopathy associated with diabetes or wounds. Many of these approaches are amenable to high throughput analysis. Further, methods are provided that allow for the identification of additional angiogenic compounds and which further treat and/or prevent foot and leg ulcers, retinopathy, and wounds. One approach involves the use of techniques in rational drug design. Accordingly, molecules that resemble identified compounds, and fragments or derivatives of these molecules, are designed and created using computer based homology searching, protein modeling, and combinatorial chemistry. For example, a database comprising nucleic acid or protein sequences corresponding to X1FX2LRX3 peptide, or fragments or derivatives of these molecules are accessed by a search program that compares the sequence to other sequences in publicly or commercially available databases so as to identify homologous ligands. By another rational approach, techniques in protein modeling (e.g., x-ray crystallography, NMR, and computer modeling) are employed to construct models of the compounds. From these models, rational drug design can be accomplished. Once the candidate compounds are designed and created, it is preferred that they are evaluated for their ability to stimulate $[Ca^{2+}]_i$ increase in endothelial cells. Approaches that evaluate the ability of a candidate and resultant induction of blood vessel formation may be carried out using a variety of assays such as Matrigel assay.

Variant and Mutant Polypeptides

To improve or alter the characteristics of the polypeptide, amino acid engineering may be employed. Recombinant DNA technology known to those skilled in the art can be used to create novel mutant polypeptides including single or multiple amino acid substitutions, deletions, additions, or fusion proteins. Similar mutant polypeptides can also be produced by chemical synthesis, especially for short peptides. Such modified polypeptides can show, e.g., increased/decreased activity or increased/decreased stability. In addition, they may be purified in higher yields and show better solubility than the corresponding natural polypeptide, at least under certain purification and storage conditions.

The compounds resembling X1FX2LRX3 peptide, and fragments or derivatives of these molecules (e.g., X1FX2LRX3 peptide mimics) not only include those molecules containing as a primary amino acid sequence all or part of the amino acid sequence of aniogenic peptide, and fragments or derivatives of these molecules found in nature but also altered sequences in which functionally equivalent amino acid residues are substituted for residues within the sequence resulting in a silent change. Accordingly, one or more amino acid residues within the sequence of angiogenic peptide, and fragments or derivatives of these molecules can be substituted by another amino acid of a similar polarity that acts as a functional equivalent, resulting in a silent alteration. Substitutes for an amino acid within the sequence can be selected from other members of the class to which the amino acid belongs. For example, the non-polar (hydrophobic) amino acids include alanine, leucine, isoleucine, valine, proline, phenylalanine, tryptophan, and methionine. The uncharged polar neutral amino acids include glycine, serine, threonine, cysteine, tyrosine, asparagine and glutamine. The positively charged (basic) amino acids include arginine, lysine, and histidine. The negatively charged (acidic) amino acids include aspartic acid and glutamic acid. The aromatic amino acids include phenylalanine, tryptophan, and tyrosine. In other aspects of the invention, X1FX2LRX3 peptide, and fragments or derivatives of these molecules, which are differentially modified during or after translation, e.g., by phosphorylation, glycosylation, cross-linking, acylation, proteolytic cleavage, linkage to an antibody molecule, membrane molecule, or other ligand, are contemplated. Accordingly, the protein sequence corresponding to X1FX2LRX3 peptide, or a fragment or derivative of these molecules can be compared to known sequences. The candidate compounds having greater than or equal to X1FX2LRX3 peptide are identified and are subsequently examined using calcium mobilization assay.

Mimetics

Peptides for use in aspects of the invention can also be modified, e.g., the peptides can have substituents not normally found on a peptide or the peptides can have substituents that are normally found on the peptide but are incorporated at regions of the peptide that are not normal. The peptides for use in aspects of the invention can be acetylated, acylated, or aminated, for example. Substituents which can be included on the peptide so as to modify it include, but are not limited to, H, alkyl, aryl, alkenyl, alkynl, aromatic, ether, ester, unsubstituted or substituted amine, amide, halogen or unsubstituted or substituted sulfonyl or a 5 or 6 member aliphatic or aromatic ring. A "SFKLRY peptide mimic" is a compound that resembles the SFKLRY peptide. SFKLRY peptide mimics can be peptidomimetics, peptides, modified peptides, and derivatized peptides.

Additional compound derivatives include peptidomimetics that resemble a polypeptide of interest. The naturally occurring amino acids employed in the biological production of peptides all have the L-configuration. Synthetic peptides can be prepared employing conventional synthetic methods, utilizing L-amino acids, D-amino acids, or various combinations of amino acids of the two different configurations. Synthetic compounds that mimic the conformation and desirable features of a particular peptide, e.g., an oligopeptide, once such peptide has been found, but that avoids the undesirable features, e.g., flexibility (loss of conformation) and bond breakdown are known as "peptidomimetics".

In general, the design and synthesis of a peptidomimetic involves starting with the sequence of the peptide and the conformation data (e.g., geometry data, such as bond lengths and angles) of a desired peptide (e.g., the most probable simulated peptide), and using such data to determine the geometries that should be designed into the peptidomimetic. Numerous methods and techniques are known in the art for performing this step, any of which could be used.

While the definition of a peptide mimetic characterizes a mimetic as a non-peptide ligand, many structures exist that are somewhere in between a true peptide, which is composed of natural amino acids, and a peptide mimetic. The debate on what constitutes a peptide mimetic is still ongoing, however a person of skill in the art is able to distinguish between a mimetic and a peptide. Peptide mimetics can generally be considered as improved versions of peptides. Chemical modifications on a peptide, such as the reduction of a peptide bond, can increase its enzymatic stability. Incorporating unnatural amino acids can also enhance both activity and selectivity of the peptide. The more a peptide is altered structurally and/or chemically, the more it becomes a true peptide mimetic. Peptide mimetics including peptides, proteins, and derivatives thereof, such as peptides containing non-peptide organic moieties, synthetic peptides which may or may not contain amino acids and/or peptide bonds, but retain the structural and functional features of a peptide ligand, and peptoids and oligopeptoids which are molecules comprising N-substituted glycine, such as those described by Simon et al., *Proc. Natl. Acad. Sci. USA* 89:9367 (1992); and antibodies, including anti-idiotype antibodies.

In another aspect of the invention, the inventive compound of the invention may be made by synthetically introducing a variety of optional compounds, such as scaffolds, turn mimetics, and peptide-bound replacements. Syntheses of amino acids to the use of a variety of linear and heterocyclic scaffolds in place of the peptide backbone may be used. Chemical procedures and methods include the transient protection of charged peptides as neutral prodrugs for improved blood-brain penetration and the replacement of peptide bonds with groups such as heterocyclic rings, olefins and fluoroolefins, and ketomethylenes.

In an embodiment of the invention, the mimetic is highly specific to its target and has low toxicity and is directed to peptide mimetics that cross the skin barrier so as to enhance the healing of wounds. Therefore, a compound that is modified so that the compound is able to cross skin barrier is encompassed by the present invention.

Pharmaceutical Composition

As used herein, "carriers" include pharmaceutically acceptable carriers, excipients, or stabilizers which are nontoxic to the cell or mammal being exposed thereto at the dosages and concentrations employed. Often the pharmaceutically acceptable carrier is an aqueous pH buffered solution. Examples of pharmaceutically acceptable carriers include without limitation buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

As used herein, "effective amount" is an amount sufficient to effect beneficial or desired clinical or biochemical results. An effective amount can be administered one or more times. For purposes of this invention, an effective amount of an inhibitor compound is an amount that is sufficient to palliate, ameliorate, stabilize, reverse, slow or delay the progression of the disease state. In a preferred embodiment of the invention, the "effective amount" is defined as an amount of compound capable of evoking the response in a given set of experiment.

As used herein, "subject" is a vertebrate, preferably a mammal, more preferably a human.

As used herein, the term, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" refers to both therapeutic treatment and prophylactic or preventative measures. Those in need of treatment include those already with the disorder as well as those in which the disorder is to be prevented. "Palliating" a disease means that the extent and/or undesirable clinical manifestations of a disease state are lessened and/or the time course of the progression is slowed or lengthened, as compared to a situation without treatment.

The discovery of several new angiogenic peptides is provided in this disclosure. These pharmaceuticals can be delivered by any conventional route including, but not limited to, transdermal, topical, parenteral, gastrointestinal, transbronchial, and transalveolar. Embodiments of the invention also include biotechnological tools, prophylactics, therapeutics, and methods of use of the foregoing, for the study, treatment, and/or prevention of foot and leg ulcers and retinopathy associated with diabetes, wounds, and skin-ageing.

The formulation of therapeutic compounds is generally known in the art and reference can conveniently be made to Remington's Pharmaceutical Sciences, 17th ed., Mack Publishing Co., Easton, Pa., USA. For example, from about 0.05 µg to about 20 mg per kilogram of body weight per day may be administered. Dosage regime may be adjusted to provide the optimum therapeutic response. For example, several divided doses may be administered daily or the dose may be proportionally reduced as indicated by the exigencies of the therapeutic situation. The active compound may be administered in a convenient manner such as by the oral, intravenous (where water soluble), intramuscular, subcutaneous, intra nasal, intradermal or suppository routes or implanting (eg using slow release molecules by the intraperitoneal route or by using cells e.g. monocytes or dendrite cells sensitised in vitro and adoptively transferred to the recipient). Depending on the route of administration, the peptide may be required to be coated in a material to protect it from the action of enzymes, acids and other natural conditions which may inactivate the ingredients.

For example, the low lipophilicity of the peptides will allow them to be destroyed in the gastrointestinal tract by enzymes capable of cleaving peptide bonds and in the stomach by acid hydrolysis. In order to administer peptides by other than parenteral administration, they will be coated by, or administered with, a material to prevent its inactivation. For example, peptides may be administered in an adjuvant, co-administered with enzyme inhibitors or in liposomes. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water CGF emulsions as well as conventional liposomes.

The active compounds may also be administered parenterally or intraperitoneally. Dispersions can also be prepared in glycerol liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, chlorobutanol, phenol, sorbic acid, theomersal and the like. In many cases, it will be preferable to include isotonic agents, for example, sugars or sodium chloride. Prolonged absorption of the injectable compositions can be brought about by the use in the composition of agents delaying absorption, for example, aluminium monostearate and gelatin.

When the peptides are suitably protected, the active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1 by weight of active compound. The percentage of the compositions and preparations may, of course, be varied. The amount of active compound in such therapeutically useful compositions is such that a suitable dosage will be obtained. Preferred compositions or preparations according to the present invention are prepared so that an oral dosage unit form contains between about 0.1 µg and 2000 mg of active compound.

The tablets, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carrier and/or diluent" includes any and all solvents, dispersion media, coatings antibacterial and antifungal agents, isotonic and absorption delaying agents and the like. The use of such media and agents for pharmaceutically active substances is well known in the art. Except insofar as any conventional media or agent is incompatible with the active ingredient, use thereof in the therapeutic compositions is contemplated. Supplementary active ingredients can also be incorporated into the compositions.

Various delivery systems are known and can be used to administer a compound of the invention, e.g., encapsulation in liposomes, microparticles, microcapsules, receptor-mediated endocytosis. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

Cosmetic Composition

As used herein, "cosmetically acceptable" means that the ingredients described are suitable for use in contact with tissues (e.g., the skin or hair) without undue toxicity, incompatibility, instability, irritation, allergic response, or the like.

As used herein, "effective amount" means an amount sufficient to improving human aged skin, such as wrinkle and darkening, but low enough to avoid serious side effects. The safe and effective amount of the composition will vary with the area being treated, the age and skin type of the end user, the duration and nature of the treatment, the specific ingredient, or composition employed, the particular cosmetically acceptable carrier utilized, and like factors.

In one embodiment, the topical composition further contains another cosmetically active agent in addition to the polymer. What is meant by a "cosmetically active agent" is a compound (e.g., a synthetic compound or a compound isolated from a natural source or a natural extract) that has a cosmetic or therapeutic effect on the skin or hair, including, but not limiting to, anti-acne agents, shine control agents, anti-microbial agents, anti-inflammatory agents, sunscreens, photoprotectors, antioxidants, keratolytic agents, detergents/surfactants, moisturizers, nutrients, vitamins, energy enhancers, anti-perspiration agents, astringents, deodorants, firming agents, anti-callous agents, and agents for hair and/or skin conditioning.

The present invention is further explained in more detail with reference to the following examples. These examples, however, should not be interpreted as limiting the scope of the present invention in any manner.

Example 1

Materials and Methods for FPRL1 Antagonist Peptide Characterization 1.1. Materials Fura-2 pentaacetoxymethylester (Fura-2-AM) and 1,2-bis (2-aminophenoxy)ethane-N,N,N',N'-tetraacetoxymethyl ester (BAPTA-AM) were purchased from Molecular Probes (Eugene, Oreg.). Pertussis toxin (PTX), U73122 and U73433 were from Calbiochem (San Diego, Calif.). Matrigel was from Becton Dickinson (Bedford, Mass.). Recombinant human VEGF and anti-VEGF neutralizing antibody were from R&D systems (Minneapolis, Minn.). Peptides were synthesized by Peptron Inc. (Korea). PS-SPCLs were prepared in the Peptide Library Support Facility at Pohang University of Science and Technology (Korea), as previously described (S. H. Baek, et al, *J Biol Chem* 271 (1996), pp. 8170-8175; R. A. Houghten, et al., *Nature* 354 (1991), pp. 84-86).

1.2. Cell Culture

MS-1 cells and B16F1 murine melanoma cells were grown in DMEM containing 10% FBS at 37° C. in a humidified incubator supplied with 95% air and 5% $CO_2$. HUVECs were prepared from fresh human umbilical cords by collagenase digestion as previously described (E. A. Jaffe, et al., *J Clin Invest* 52 (1973), pp. 2745-2756), and maintained in 20% FBS-containing M-199 medium. All HUVECs used in this study are no older than passage five. Human normal fibroblast cells were purchased from American Type Culture Collection (ATCC). The cells were cultured in DMEM containing 10% FBS and 1% antibiotics at 37° C. in a humidified atmosphere of 5% $CO_2$. The cells were then subcultured with 0.05% trypsin-0.53 mM EDTA after replacing with a fresh medium every two or three days.

1.3. Iterative Screening of the PS-SPCLs Using $[Ca^{2+}]_i$ Mobilization Assay in MS-1 Cells Cells were incubated with 4 μM Fura-2 AM and 250 μM sulfinpyrazone in serum-free DMEM medium at 37° C. for 30 min with continuous stirring. The cells were then washed with Locke's solution (M. Faehling, et al., *FASEB J* 16 (2002), pp. 1805-1807) and diluted to $2 \times 10^6$ cells/mL. 50 μL aliquots of cell suspension were added to each well of a 96-well plate, and the change in fluorescence ratio was determined at dual excitation wavelengths of 340 and 380 nm and emission wavelength of 500 nm following addition of peptides. Plates were read immediately following the addition of peptide pools, resulting in a time delay of approximately 5 s between peptide addition and detection by the FLEXstation (Molecular Devices). Negative and positive controls were run simultaneously with test samples to ensure that all samples were subjected to identical conditions. The calibration of the fluorescence ratio in terms of $[Ca^{2+}]_i$ was performed according to Grynkiewicz et al. *J Biol Chem* 260 (1985), pp. 3440-3450.

1.4. [$^3$H]-Thymidine Incorporation Assay

HUVECs were plated onto 24-well culture dishes at a density of $2 \times 10^4$ cells/well and permitted to attach overnight. After 12 h of serum starvation, the cells were treated with or without the indicated concentrations of SFKLRY-$NH_2$ (SEQ ID NO: 2) for 48 h. Cells were labeled with [$^3$H]-thymidine (25 mCi/mmol; Amersham, Aylesbury, United Kingdom) for 4 h before the assay (M. Guidoboni, et al., *Cancer Res* 65 (2005), pp. 587-595). Unincorporated [$^3$H]-thymidine was removed by washing with 10% trichloroacetic acid, and then incorporated [$^3$H]-thymidine was extracted in 0.2 M NaOH and 0.1% SDS at 37° C. for 1 h. The radioactivities in the cells were counted with a liquid scintillation counter (Beckman Instruments, Fullerton, Calif.).

1.5. Tube Formation Assay

As described previously in M. S. Lee, et al., *J Immunol* 177 (2006), pp. 5585-5594, HUVECs were seeded on a layer of previously polymerized Matrigel with SFKLRY-NH$_2$ (SEQ ID NO: 2), its scrambled sequence FYSRLK-NH$_2$, S1P or VEGF in the presence or absence of VEGF neutralizing antibody. After 24 h of incubation, changes in cell morphology were observed through a phase-contrast microscope and photographed. To measure the formation of the capillary network, the total tube length per field was measured at 40× magnification with the scale. Three different fields were analyzed per well.

1.6. Wounding Migration Assay

To determine the effects of SFKLRY-NH2 (SEQ ID NO: 2) on HUVEC migration, in vitro wound healing repair assay was performed as previously described in M. S. Lee, et al., *J Immunol* 177 (2006), pp. 5585-5594. Briefly, HUVECs, plated on 35-mm culture dishes at 90% confluence, were wounded with a 2-mm-wide razor blade and marked at the injury line. After wounding, the cells were washed with serum-free medium and further incubated in M199 containing 1% serum and/or the indicated amount of SFKLRY-NH$_2$ (SEQ ID NO: 2). HUVECs were allowed to migrate for 16 h, rinsed with serum-free medium, fixed with absolute methanol and stained with Giemsa. Migration was quantified by counting the number of cells that moved beyond the injury line.

1.7. Aortic Ring Assay

The method developed by Nicosia and Ottinetti in *In Vitro Cell Dev Biol* 26 (1990), pp. 119-128 was used with some modifications. Aortas were harvested from 6-week-old Sprague-Dawley rats. After removing the surrounding fibroadipose tissues, the rings were immersed in Matrigel in wells within culture dishes. The aortic rings were cultured (5% CO$_2$, 37° C.) in serum-free M199 containing SFKLRY-NH$_2$ (SEQ ID NO: 2), S1P, FYSRLK-NH$_2$, or VEGF in the presence or absence of PTX or U73122. On day 7, sprouting from aortic explants was measured.

1.8. RT-PCR Analysis

Total RNA from HUVECs was isolated using the easy-BLUE™ total RNA extraction kit (Intron Biotechnology, Inc.) according to the manufacturer's instructions. Single-stranded cDNA was synthesized by Moloney murine leukemia virus reverse transcriptase (MMLV-RT) with 3 μg of DNA-free total RNA and oligo(dT)$_{15}$ primer (Promega). The sequences of the primers used were: human VEGF (150-bp product): forward, 5'-GAGGAGGGCAGAATCATCACG-3' (SEQ ID NO:25); reverse, 5'-ATCGCATGAGGGGCA-CACAGG-3' (SEQ ID NO:26). PCR products were electrophoresed on a 2% agarose gel and visualized by ethidium bromide staining.

1.9. Conditioned Medium and ELISA

Conditioned medium was generated as follows: 80% confluent HUVECs in six-well dishes were fed with 2 mL per dish of serum-free M199 and incubated for indicated times. The collected medium was centrifuged to remove any residual cells and frozen at −80° C. Enzyme-linked immunosorbent assay (ELISA) analyses for VEGF (R&D systems) were performed following the manufacturer's instructions.

1.10. Statistical Analysis

The data are represented as mean±S.D. Statistical comparisons between groups were performed using Sigma Plot followed by Student's t-test.

Example 2

2.1. Identification of Peptides that Induce [Ca$^{2+}$]$_i$ Increase in MS-1 Cells To identify peptides that stimulate intracellular calcium mobilization in murine endothelial cells (MS-1 cells), the inventors screened 114 pools of C-terminally amidated synthetic hexapeptides. The results of the initial screening of the peptide libraries in MS-1 cells are shown in FIG. 1A to 1F.

FIG. 1A to 1F show the initial screening of the PS-SPCLs for peptides increasing intracellular calcium in MS-1 cells. Each panel indicates the results obtained with the peptide pools with known amino acids at each of the six positions of the hexapeptides. The six positions were individually defined (e.g., O1, O2) by one of the 19 L-amino acids. The remaining five positions consist of mixtures (X) of the 19 L-amino acids (excluding cystein). The library consists of 114 peptide pools; the PS-SPCL in total is made up of 47,045,881 different peptides. [Ca$^{2+}$]$_i$ increase was measured fluorometrically using Fura-2/AM as described in Example 1. This result represents one of three independent experiments.

The most active amino acids at each position were: Ser (S) and Thr (T) in the first position; Phe (F) in second; Ile (I), Lys (K), and Arg (R) in third; Leu (L) in fourth; Arg (R) in fifth; and Arg (R), Phe (F), Trp (W), Tyr (Y), and His (H) in sixth.

Based on the results obtained from the initial screening of the peptide libraries, SFKLRY-NH2 (SEQ ID NO: 2), was chosen and synthesized as a prototype peptide for further analysis. C-terminally amidated form of SFKLRY-NH2 (SEQ ID NO: 2) displayed more potent activity than carboxylated peptide (SFKLRY-COOH) and modification at the first amino terminal residue (deletion or replacement with D-form amino acid) led to complete loss of intracellular calcium-mobilizing activity, suggesting that intracellular calcium-mobilizing activity is sequence-specific and also the amino terminal residue is more critical than the C-terminal residue for activity. Moreover, the results of other hexapeptides also correlated with initial screening results (Table 1). Many peptide ligands exist in the C-terminally amidated form and this modification is critical for the expression of activity in some cases (Y. In, M. Fujii, et al., *Acta Crystallogr B* 57 (2001), pp. 72-81); thus, our peptide shares characteristics as a ligand for certain receptor(s) in the cells.

TABLE 1

EC$_{50}$ of peptides tested on MS-1 cells as determined from dose-dependent changes in intracellular Ca$^{2+}$. The peptide sequences are shown along with EC$_{50}$ and S.E. derived from three experiments

| SEQ ID NO | Sequence | Mean EC$_{50}$ (μM) | S.E.M. |
|---|---|---|---|
| 1 | SFKLRY-COOH | >10 | N/A |
| 2 | SFKLRY-NH$_2$ | 1.21 | 0.01 |

TABLE 1-continued

EC$_{50}$ of peptides tested on MS-1 cells as determined from dose-dependent changes in intracellular Ca$^{2+}$. The peptide sequences are shown along with EC$_{50}$ and S.E. derived from three experiments

| SEQ ID NO | Sequence | Mean EC$_{50}$ (µM) | S.E.M. |
|---|---|---|---|
| 3 | sFKLRY-NH$_2$(d-form) | N/D | N/A |
| 4 | SfKLRY-NH$_2$(d-form) | N/D | N/A |
| 5 | SFkLRY-NH$_2$(d-form) | N/D | N/A |
| 6 | SFKlRY-NH$_2$(d-form) | >100 | N/A |
| 7 | SFKLrY-NH$_2$(d-form) | >100 | N/A |
| 8 | SFKLRy-NH$_2$(d-form) | 1.14 | 0.09 |
| 9 | FKLRY-NH$_2$ | N/D | N/A |
| 10 | KLRY-NH$_2$ | N/D | N/A |
| 11 | LRY-NH$_2$ | N/D | N/A |
| 12 | SFKLR-NH$_2$ | 6.19 | 0.84 |
| 13 | SFKL-NH$_2$ | >50 | N/A |
| 14 | SFK-NH$_2$ | N/D | N/A |
| 15 | SFRLRY-NH$_2$ | 0.97 | 0.14 |
| 16 | SFKLRR-NH$_2$ | 2.66 | 0.36 |
| 17 | SFILRY-NH$_2$ | 0.99 | 0.2 |
| 18 | SFILRR-NH$_2$ | 0.97 | 0.09 |
| 19 | SFKLRW-NH$_2$ | 2.37 | 0.4 |
| 20 | SFILRW-NH$_2$ | 1.98 | 0.03 |
| 21 | SFKLRF-NH$_2$ | 3.16 | 0.91 |
| 22 | SFILRF-NH$_2$ | 2.01 | 0.18 |
| 23 | SFKLRH-NH$_2$ | 3.6 | 0.11 |
| 24 | TFKLRY-NH$_2$ | 3.87 | 1.15 |

Note:
In SEQ ID NOs: 3 to 8, the small letters are referred to an amino acid in D-form.

2.2. SFKLRY-NH2 (SEQ ID NO: 2) Induces [Ca$^{2+}$]$_i$ Increase, Proliferation, Migration, and Formation of Tubular-Like Structures in HUVECs To verify that SFKLRY-NH2 (SEQ ID NO: 2) induces [Ca$^{2+}$]$_i$ increase in human endothelial cells, intracellular Ca$^{2+}$ mobilization in primary cultured human umbilical vein endothelial cells (HUVECs) were measured. Treatment with SFKLRY-NH2 (SEQ ID NO: 2) induced [Ca$^{2+}$]$_i$ increase in HUVECs with the half-maximal effect at 1.4±0.15 µM. (data not shown), although the scrambled sequence, FYSRLK-NH$_2$ (10 µM), did not trigger Ca$^{2+}$ mobilization in HUVECs. The dose-response curve for Ca$^{2+}$ release triggered by the peptide was very similar to that observed in mouse endothelial cell lines (FIG. 2A-2C).

Figure 2A:
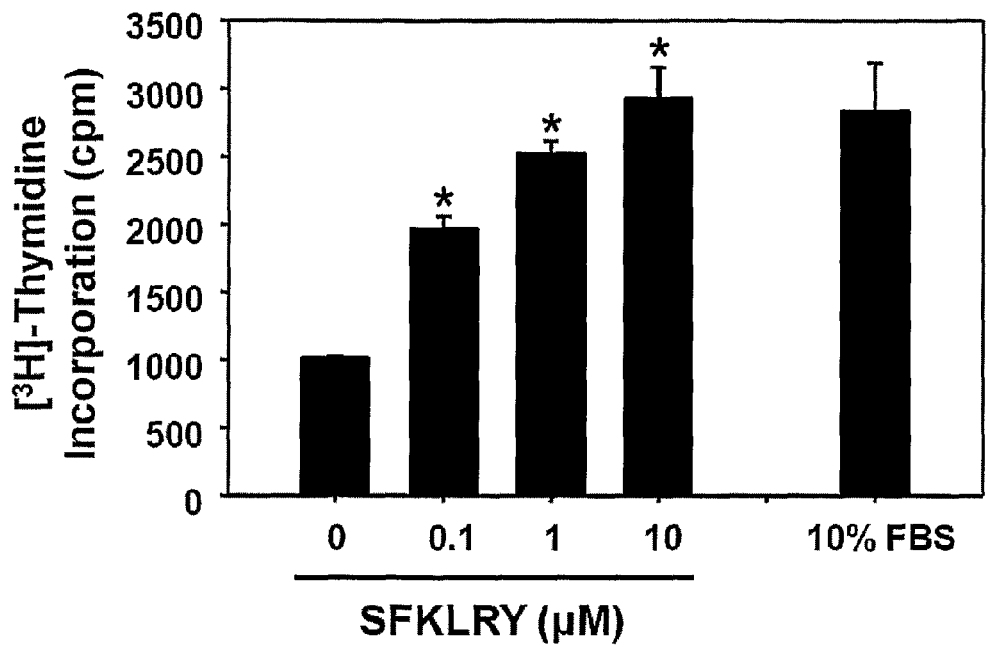
FIGS. 2A-2C show SFKLRY-NH$_2$ (SEQ ID NO: 2) induces proliferation, migration, and tube formation in HUVECs. Cells were treated with different concentration of SFKLRY-NH$_2$ (SEQ ID NO: 2) (0.1-10 μM). After 48 h of incubation, the activity of DNA synthesis was counted with a liquid scintillation counter. Bars represent the means±S.D. of three independent experiments. *P<0.05. (B) Mobility of HUVECs by different doses of SFKLRY-NH$_2$ (SEQ ID NO: 2). After wounding, HUVECs were incubated with indicated concentration of SFKLRY-NH$_2$ (SEQ ID NO: 2) (0.1-10 μM) for 16 h and then migrated HUVECs beyond the reference line were counted. Values are representative of three independent experiments performed in duplicates (means±S.D.). *P<0.05. (C) The effect of SFKLRY-NH$_2$ (SEQ ID NO: 2) on tube formation of HUVECs. HUVECs were seeded on growth factor-reduced Matrigel and treated with SFKLRY-NH$_2$ (SEQ ID NO: 2) (1 μM), FYSRLK-NH$_2$ (10 μM), and S1P (100 nM) for comparison. After incubation for 24 h, the tubular-like structures were photographed and the length of tube formation was measured. Values are representative of three independent experiments performed in duplicates (means±S.D.). *P<0.05.
Figure 2B:
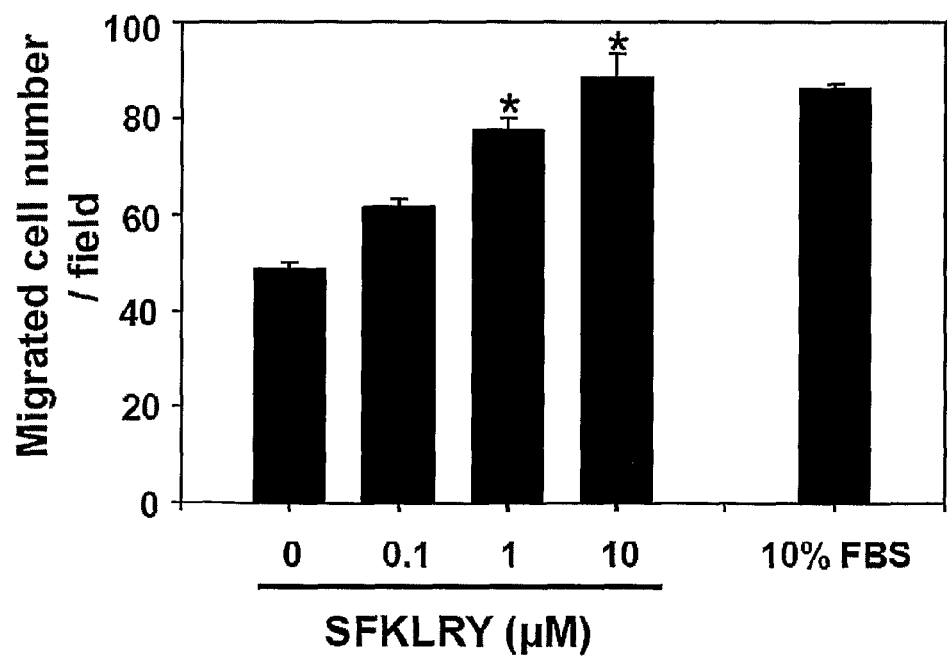
Figure 2C:
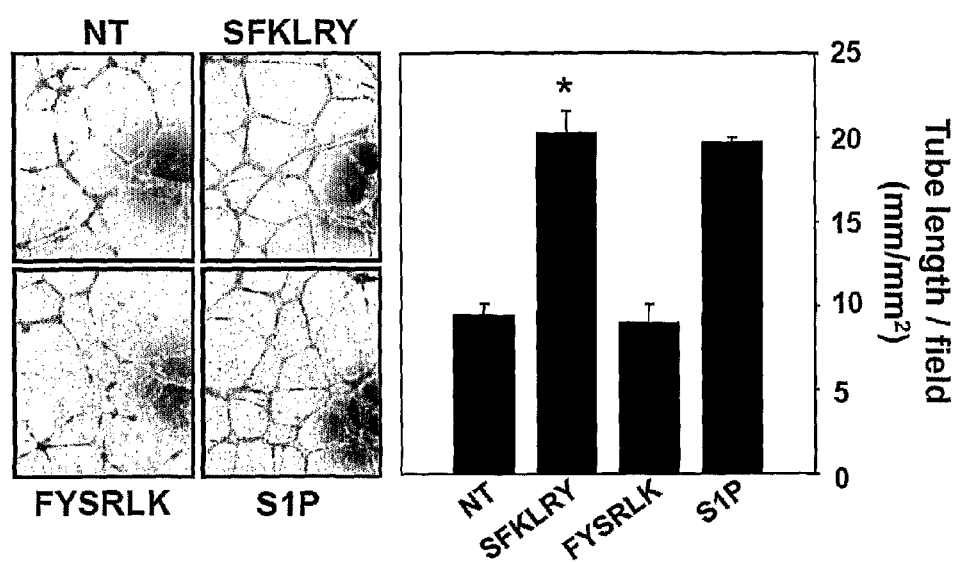

FIGS. 2A-2C show SFKLRY-NH$_2$ (SEQ ID NO: 2) induces proliferation, migration, and tube formation in HUVECs. (A) The effect of SFKLRY-NH$_2$ on proliferation of HUVECs. Cells were treated with different concentration of SFKLRY-NH$_2$ (SEQ ID NO: 2) (0.1-10 µM). After 48 h of incubation, the activity of DNA synthesis was counted with a liquid scintillation counter. Bars represent the means±S.D. of three independent experiments. *P<0.05. (B) Mobility of HUVECs by different doses of SFKLRY-NH$_2$ (SEQ ID NO: 2). After wounding, HUVECs were incubated with indicated concentration of SFKLRY-NH$_2$ (SEQ ID NO: 2) (0.1-10 µM) for 16 h and then migrated HUVECs beyond the reference line were counted. Values are representative of three independent experiments performed in duplicates (means±S.D.). *P<0.05. (C) The effect of SFKLRY-NH$_2$ (SEQ ID NO: 2) on tube formation of HUVECs. HUVECs were seeded on growth factor-reduced Matrigel and treated with SFKLRY-NH$_2$ (SEQ ID NO: 2) (1 µM), FYSRLK-NH$_2$ (10 µM), and S1P (100 nM) for comparison. After incubation for 24 h, the tubular-like structures were photographed and the length of tube formation was measured. Values are representative of three independent experiments performed in duplicates (means±S.D.). *P<0.05.

The process of angiogenesis is complex and involves several distinct steps, including extracellular matrix degradation, proliferation, migration, and morphological differentiation of endothelial cells to form tubes (F. Bussolino, et al., *Trends Biochem Sci* 22 (1997), pp. 251-256). To determine whether SFKLRY-NH2 (SEQ ID NO: 2) induces angiogenesis, the ability of SFKLRY-NH$_2$ (SEQ ID NO: 2) as an angiogenic stimulus has been assessed in in vitro angiogenesis models. The present inventors firstly examined the effect of SFKLRY-NH2 (SEQ ID NO: 2) on aspects of angiogenic cascades: proliferation in HUVECs.

When the effect of SFKLRY-NH2 (SEQ ID NO: 2) on DNA synthesis of HUVECs was assessed using [$^3$H]-thymidine incorporation assay, SFKLRY-NH2 (SEQ ID NO: 2) promoted the proliferative activity of HUVECs in a dose-dependent manner and increased DNA synthesis of HUVECs about 2.5-fold at 1 µM. The proliferative activity of the peptide at 10 µM is comparable with that of 10% FBS (FIG. 2A).

Since angiogenesis is highly dependent on endothelial cell motility, the present inventors next examined the effect of SFKLRY-NH2 (SEQ ID NO: 2) on HUVEC migration in an in vitro wounding migration assay. As shown in FIG. 2B, the migratory activity of HUVECs was enhanced by addition of SFKLRY-NH2 (SEQ ID NO: 2) in a dose-dependent manner with near maximal activity at 10 µM. The migratory activity at 10 µM of SFKLRY-NH2 (SEQ ID NO: 2) was 1.6-fold increase over the control (vehicle or no treatment), and the effect of SFKLRY-NH2 (SEQ ID NO: 2) was comparable with 10% FBS which is the known stimuli of HUVEC migration.

To provide further evidence for a functional role of SFKLRY-NH2 (SEQ ID NO: 2) in endothelial cells, the effect of SFKLRY-NH2 (SEQ ID NO: 2) on morphological differentiation in HUVECs was examined in an in vitro tube formation assay (FIG. 2C). While control cells aggregated and formed clusters, HUVECs treated with SFKLRY-NH2 (SEQ ID NO: 2) (10 µM) showed morphological changes such as elongation and lining that led to network formation. Tube-forming activity of SFKLRY-NH2 (SEQ ID NO: 2) (20.25±1.31) was over two-fold higher than that of control cells (9.4±0.67) and the activity of 10 µM SFKLRY-NH2 (SEQ ID NO: 2) was similar to that of 100 nM S1P (19.69±0.32), while the scrambled sequence, FYSRLK-NH$_2$ with 10 µM (8.96±1.14), had no effect on morphological differentiation of HUVECs (FIG. 2C). These results support the sequence-specific properties of SFKLRY-NH2 (SEQ ID NO: 2) for neovascularization in vitro human endothelial cell culture system.

2.3. SFKLRY-NH$_2$ (SEQ ID NO: 2)-Induced [Ca$^{2+}$]$_i$ Increase is Mediated by PTX Sensitive G Protein-PLC Signal Pathway To delineate the SFKLRY-NH2 (SEQ ID NO: 2)-mediated signaling pathway in endothelial cells, the present inventors explored the upstream signaling mechanisms related to increasing intracellular Ca$^{2+}$. PLC is known to generate IP3 and diacylglycerol, which activate intracellular Ca$^{2+}$ mobilization (M. J. Berridge et al., *Nature* 312 (1984), pp. 315-321; P. W. Majerus, et al., *Biochem Biophys Res Commun* 268 (2000), pp. 47-53; and Y. Nishizuka, *Science* 258 (1992), pp. 607-614). To explore the potential involvement of PLC-mediated signaling pathway in SFKLRY-NH2 (SEQ ID NO: 2)-induced Ca$^{2+}$ signaling, the effects of the PLC inhibitor, U73122 and its inactive analogue U73433, on the peptide-induced intracellular calcium mobilization were investigated.

Figure 3A:
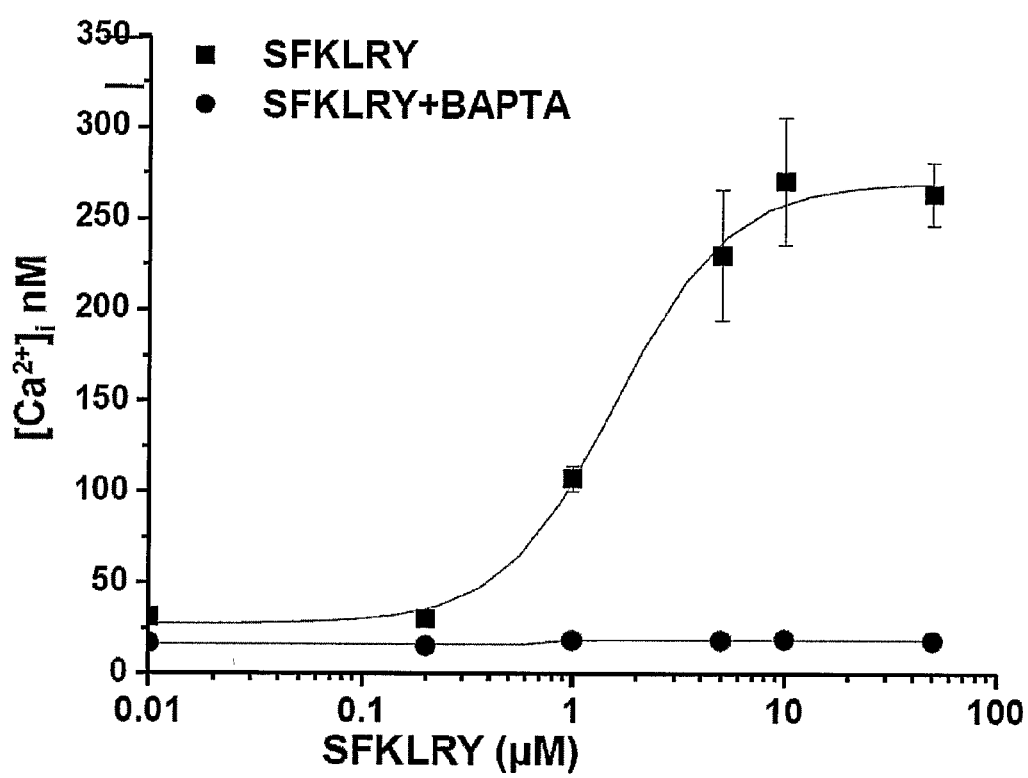
FIGS. 3A-3B show BAPTA, U73122 and PTX suppressed SFKLRY-NH$_2$-induced [Ca$^{2+}$]$_i$ increase in MS-1 cells. SFKLRY-NH$_2$ (SEQ ID NO: 2)-induced intracellular Ca2+ mobilizing activity was measured in presence and absence intracellular calcium chelator, BAPTA-AM (A), the PLC inhibitor U73122 and its inactive analogue U73433, and PTX (B). (A) The cells were pre-incubated in DMEM containing 10 μM BAPTA-AM with Fluo-4/AM for 30 min at 37° C. Cells were suspended in Ca2+-free Locke's solution containing 0.2 mM EGTA and treated with indicated concentrations of SFKLRY-NH$_2$ (SEQ ID NO: 2). The change in fluorescence intensity was determined with excitation at 488 nm and the emission at 520 nm. (B) Cells were preincubated with or without U73122 (10 μM), U73433 (10 μM) for 30 min, and PTX (100 ng/mL) for 2 h with Fura-2, respectively. Fura-2-loaded cells were then suspended in Ca2+-free Locke's solution and then treated with 1 SFKLRY-NH$_2$(SEQ ID NO: 2). The data are represent means±3 independent experiments each performed in triplicate. *P<0.05.
Figure 3B:
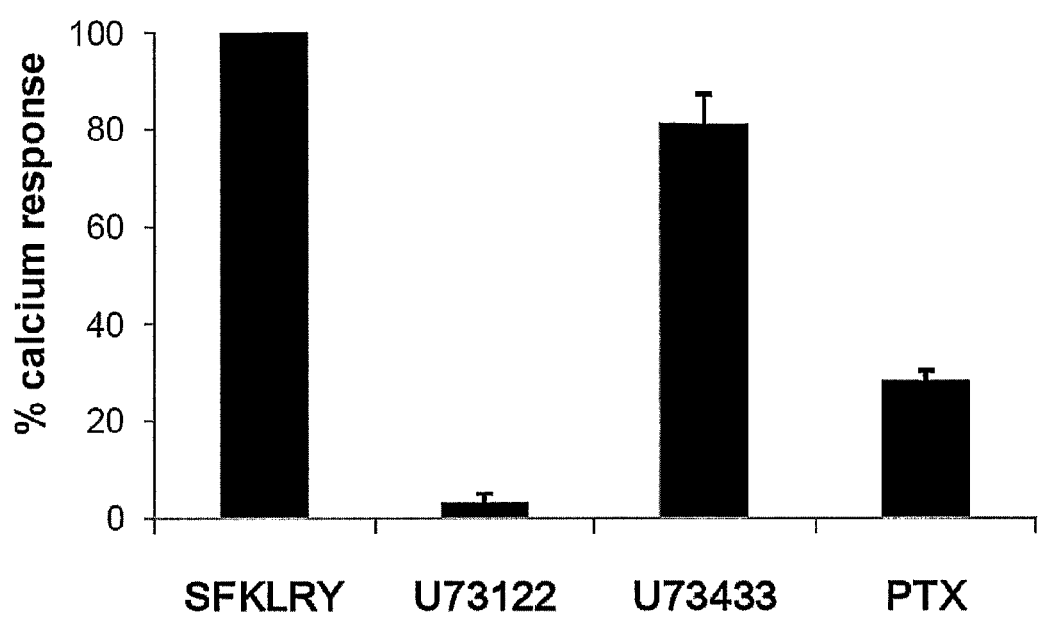

FIGS. 3A-3B show BAPTA, U73122 and PTX suppressed SFKLRY-NH$_2$-induced [Ca$^{2+}$]$_i$ increase in MS-1 cells. SFKLRY-NH$_2$ (SEQ ID NO: 2)-induced intracellular Ca$^{2+}$ mobilizing activity was measured in presence and absence intracellular calcium chelator, BAPTA-AM (A), the PLC inhibitor U73122 and its inactive analogue U73433, and PTX (B). (A) The cells were pre-incubated in DMEM containing 10 μM BAPTA-AM with Fluo-4/AM for 30 min at 37° C. Cells were suspended in Ca$^{2+}$-free Locke's solution containing 0.2 mM EGTA and treated with indicated concentrations of SFKLRY-NH$_2$ (SEQ ID NO: 2). The change in fluorescence intensity was determined with excitation at 488 nm and the emission at 520 nm. (B) Cells were preincubated with or without U73122 (10 μM), U73433 (10 μM) for 30 min, and PTX (100 ng/mL) for 2 h with Fura-2, respectively. Fura-2-loaded cells were then suspended in Ca$^{2+}$-free Locke's solution and then treated with 1 μM SFKLRY-NH$_2$ (SEQ ID NO: 2). The data are represent means±3 independent experiments each performed in triplicate. *P<0.05.

U73122 (10 μM) completely abolished the peptide-induced intracellular calcium mobilization, but U73433 (10 μM) had little inhibitory effect (FIG. 3B). Since the induction of angiogenic activity of HUVECs through G$_i$-coupled receptor-PLC-intracellular Ca$^{2+}$ signal pathway was well described (D. English, et al., *Biochim Biophys Acta* 1582 (2002), pp. 228-239; O. H. Lee, et al., *Biochem Biophys Res Commun* 268 (2000), pp. 47-53; F. Wang, et al., *J Biol Chem* 274 (1999), pp. 35343-35350), the involvement of G-proteins in the SFKLRY-NH$_2$ (SEQ ID NO: 2)-induced intracellular Ca$^{2+}$ mobilization was examined. When MS-1 cells were treated with pertussis toxin (PTX) (100 ng/mL) for 2 h prior to treatment with SFKLRY-NH2 (SEQ ID NO: 2), the peptide-dependent intracellular Ca$^{2+}$ mobilization was remarkably attenuated by PTX pretreatment as shown in FIG. 3B, indicating that the response is largely driven by PTX-sensitive G-proteins. Generally, elevated [Ca$^{2+}$]$_i$ is achieved either by Ca$^{2+}$ release from internal stores or by influx from the extracellular environment.

To determine the source of the Ca$^{2+}$ pool, the peptide-induced [Ca$^{2+}$]$_i$ increase was measured in MS-1 cells in Ca$^{2+}$-free Locke's solution containing 0.2 mM EGTA. Whereas the elevation of intracellular Ca$^{2+}$ concentration was shown in dose-dependent manner (FIG. 3A), the absence of BAPTA-AM, the depletion of intracellular Ca$^{2+}$ by preloading MS-1 cells with intracellular Ca$^{2+}$-chelator BAPTA-AM (10 μM) completely abolished the [Ca$^{2+}$]$_i$ increase, even in cells treated with the maximally effective peptide concentration (FIG. 3A). These results indicate that the SFKLRY-NH$_2$ (SEQ ID NO: 2) can trigger [Ca$^{2+}$]$_i$ increase from the intracellular Ca$^{2+}$ reservoirs and PTX-sensitive G-proteins may be involved in PLC-mediated intracellular calcium mobilization in MS-1 cells.

Figure 4:
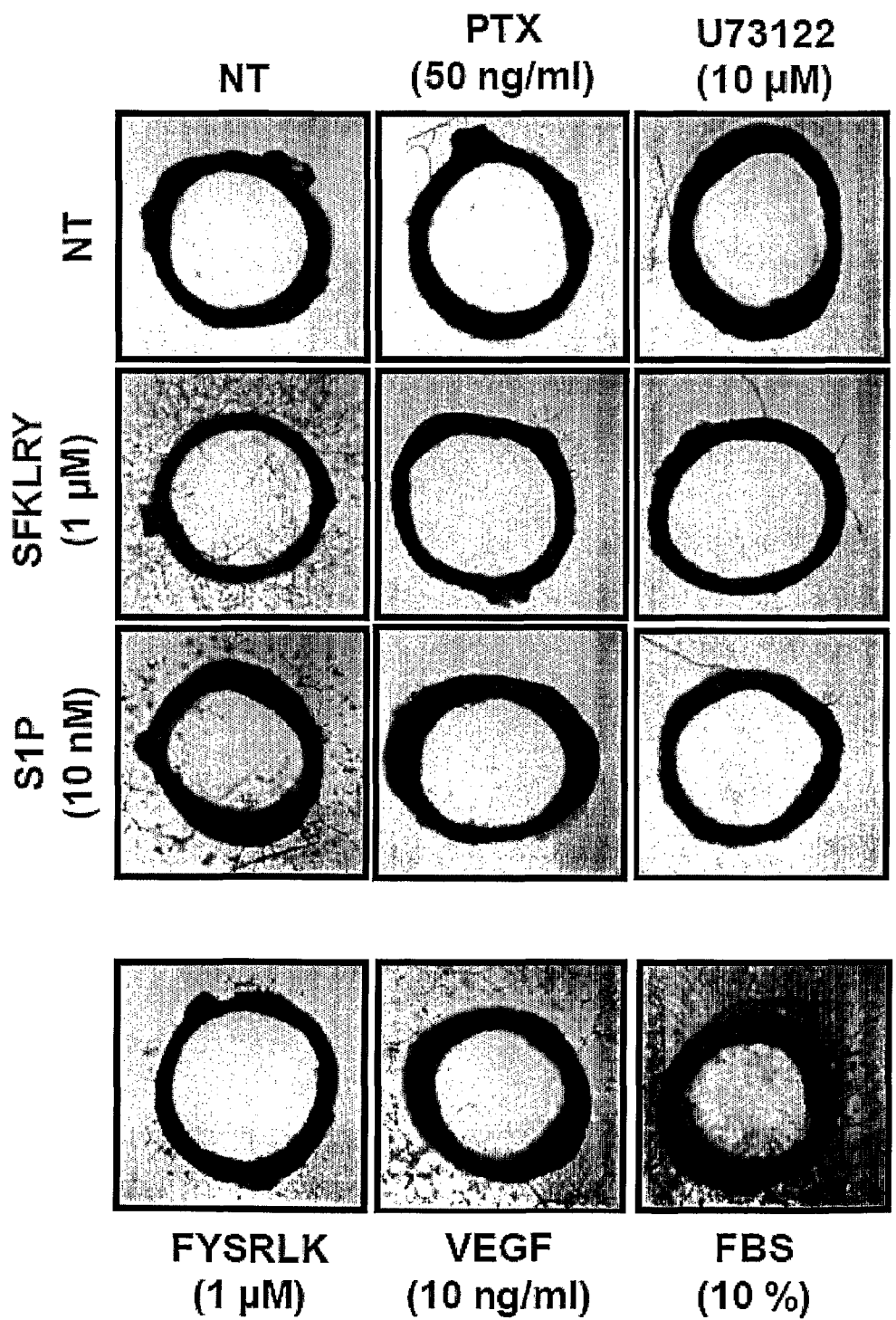
FIG. 4 shows SFKLRY-NH$_2$ (SEQ ID NO: 2) induces vessel sprouting ex vivo. Rat aortic explants in Matrigel were incubated with M-199 harboring SFKLRY-NH$_2$ (SEQ ID NO: 2) (1 μM), FYSRLK-NH2 (1 μM), S1P (10 nM), VEGF (10 ng/mL), SFKLRY-NH2 (SEQ ID NO: 2) (1 μM) with U73122 (10 μM) or PTX (50 ng/mL), or 10% FBS and photographed after incubation for 7 days. Three independent experiments were then conducted, each in duplicate.

If SFKLRY-NH2 (SEQ ID NO: 2) is supposed to bind to the membrane receptor(s) and induce intracellular Ca$^{2+}$ production, it is imperative to know the signal transduction mechanism involved in. PTX which inhibits G proteins by ADP-ribosylation of α subunit, largely attenuated intracellular Ca$^{2+}$ increase (FIG. 3B) and significantly abolished the activity of outgrowth of endothelial cells from vessel explants in a rat aorta ring by SFKLRY-NH2 (SEQ ID NO: 2) (FIG. 4). Thus, our data suggest that mediation of PTX-sensitive G protein is an important signal in the actions of SFKLRY-NH2 (SEQ ID NO: 2)-induced angiogenesis. Signaling followed by G proteins leads to a variety of cellular responses, including activation of phospholipase C which hydrolyses PIP$_2$ and yield subsequent formation of DAG and IP$_3$ mediating the release of intracellular calcium from intracellular Ca$^{2+}$ stores. A variety of hormones, growth factors, and various neurotransmitters employ this signaling pathway (M. J. Berridge., *Nature* 312 (1984), pp. 315-321; P. W. Majerus, et al., *Cell* 63 (1990), pp. 459-465; Y. Nishizuka, *Science* 258 (1992), pp. 607-614). Phospholipase C inhibitor, U73122 abolished the SFKLRY-NH2 (SEQ ID NO: 2)-initiated intracellular calcium mobilization (FIG. 3B), thus showing that [Ca$^{2+}$] increase depends on the activation of PLC. Based on these results, it is likely that SFKLRY-NH2 (SEQ ID NO: 2) triggers its response through the activation of PTX sensitive G-protein coupled cell surface receptor(s) followed by PLC-mediated intracellular calcium mobilization from the internal stores (FIG. 3A).

Thus, our data suggest that mediation of pertussis toxin-sensitive G protein is important signal in the actions of SFKLRY-NH2 (SEQ ID NO: 2)-induced angiogenesis, which is rather the implication of the receptor(s) classified into GPCR than direct G protein activator such as mastoparan (R. Weingarten, *J Biol Chem* 265 (1990), pp. 11044-11049). Mastoparan is amphiphilic peptide and has intracellular Ca$^{2+}$ mobilizing activity in a variety of cells including immune and neuronal cell lines (J. F. Klinker, et al., *Biochem J* 304 (1994), pp. 377-383; T. Murayama, et al., *J Cell Physiol* 169 (1996), pp. 448-454). However, SFKLRY-NH2 (SEQ ID NO: 2) is hydrophilic peptide which is difficult to penetrate cell membrane and the intracellular calcium mobilizing activity was observed in the cells such as MC3T3-E1, C6bu1, NIH/3T3, and C2C12 cells, but not in the neuronal or immune cells such as PC12 and U937 (data not shown). However, to achieve the same level of calcium response in other cells, more than 10-fold higher dose or more dose of SFKLRY-NH2 (SEQ ID NO: 2) was required. Our observation suggests that putative receptor for SFKLRY-NH2 (SEQ ID NO: 2) is widely expressed in cells of mesenchymal lineage, and the action of the SFKLRY-NH2 (SEQ ID NO: 2) is more specific in endothelial cells.

Recently, several reports described the implication of the activation of G-protein-coupled receptors (GPCRs) followed by turning-on of PLC-Ca$^{2+}$ signaling pathway in the regulation of angiogenic process (D. English, et al., *Biochim Biophys Acta* 1582 (2002), pp. 228-239; D. S. Gelinas, et al., *Br J Pharmacol* 137 (2002), pp. 1021-1030; Y. M. Kim, et al., *J Biol Chem* 277 (2002), pp. 6799-6805; F. Wang, et al., *J Biol Chem* 274 (1999), pp. 35343-35350). G$_i$-coupled receptor-mediated PLC-Ca$^{2+}$ signaling pathway has been known to be important in S1P-stimulated focal adhesion formation and migration of endothelial cells (O. H. Lee, et al., *Biochem Biophys Res Commun* 268 (2000), pp. 47-53; F. Wang, et al., *J Biol Chem* 274 (1999), pp. 35343-35350). In the initial phase of neovascularization, the sprouting of endothelial cells is an essential step requiring cell proliferation, cell migration, and tube formation (W. Risau, et al., *Nature* 386 (1997), pp. 671-674). Our results showed that cell proliferation, migration, and tube formation of HUVECs were enhanced by treatment of SFKLRY-NH2 (SEQ ID NO: 2) in a dose-dependent manner (FIG. 2). In addition, the result of SFKLRY-NH2 (SEQ ID NO: 2)-stimulated outgrowth of endothelial cells from rat aortic rings in an ex vivo is similar to the result obtained by VEGF treatment (FIG. 4). The endothelial cells sprouting from vessel explants by SFKLRY-NH2 (SEQ ID NO: 2) were markedly diminished by treatment of PTX or U73122 in the accordance with the effects of those inhibitors on the peptide-induced $[Ca^{2+}]_i$ mobilization. These results imply that PTX sensitive GPCR-PLC-$Ca^{2+}$ signal pathway is indispensible for SFKLRY-NH2 (SEQ ID NO: 2)-induced endothelial cell sprouting.

2.4. Induction of Vessel Sprouting Ex Vivo by SFKLRY-NH2

To address whether SFKLRY-NH2 (SEQ ID NO: 2) plays a role in sprouting of vascular endothelial cells ex vivo, aortic rings were analyzed in the presence of various stimuli including 1 µM SFKLRY-NH2 (SEQ ID NO: 2), 10 ng/mL VEGF, 10 nM S1P, and 10% FBS. SFKLRY-NH2 (SEQ ID NO: 2) (1 µM) caused significant outgrowth of endothelial cells from vessel explants, the vessel sprouting activity was higher than those of 10 nM S1P and 10 ng/mL VEGF treatment. FIG. 4 shows SFKLRY-NH$_2$ (SEQ ID NO: 2) induces vessel sprouting ex vivo. Rat aortic explants in Matrigel were incubated with M-199 harboring SFKLRY-NH$_2$ (SEQ ID NO: 2) (1 µM), FYSRLK-NH$_2$ (1 µM), S1P (10 nM), VEGF (10 ng/mL), SFKLRY-NH$_2$ (SEQ ID NO: 2) (1 µM) with U73122 (10 µM) or PTX (50 ng/mL), or 10% FBS and photographed after incubation for 7 days. Three independent experiments were then conducted, each in duplicate.

In addition, the scrambled sequence, FYSRLK-NH$_2$ (1 µM), had negligible activity. In accordance with the effects of PTX and U73122 on $[Ca^{2+}]_i$ mobilization, the vessel sprouting activity promoted by SFKLRY-NH2 (SEQ ID NO: 2) was markedly attenuated by co-treatment with PTX (50 ng/mL) or U73122 (10 µM) (FIG. 4). Therefore, these findings indicate that PTX-sensitive-G-protein, PLC—$[Ca^{2+}]_i$ signaling pathway is involved in enhancing vessel sprouting by the peptide.

2.5. Up-Regulation of VEGF mRNA by SFKLRY-NH2 (SEQ ID NO: 2)

Figure 5A:
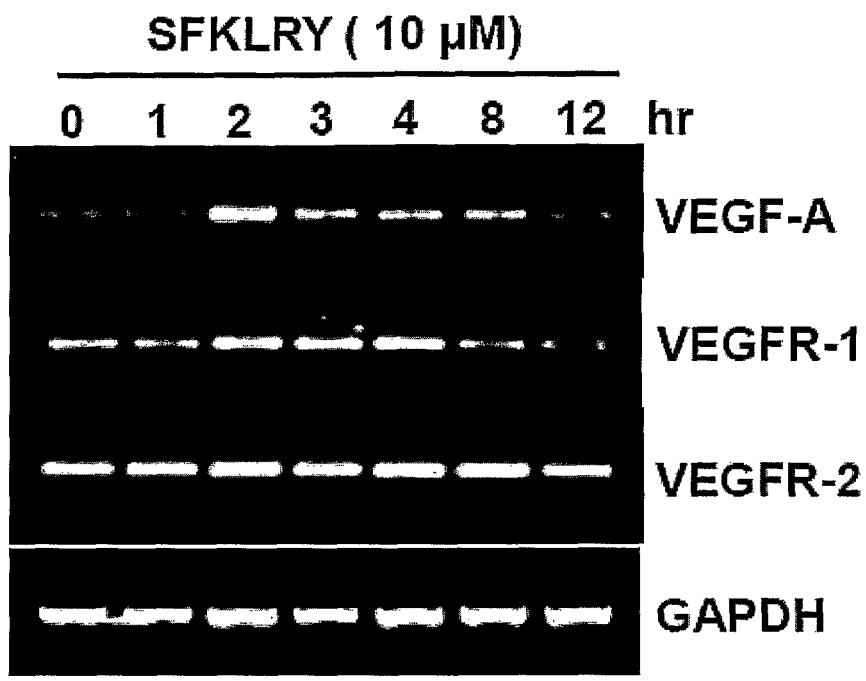
FIGS. 5A-5B show up-regulation of VEGF and VEGFR-1 mRNA by SFKLRY-NH$_2$ (SEQ ID NO: 2). RT-PCR analysis was performed on mRNA isolated from primary cultured HUVECs treated with SFKLRY-NH2 (SEQ ID NO: 2). The data presented are representative of three independent experiments. SFKLRY-NH2 (SEQ ID NO: 2) (10 μM) was treated for 0, 1, 2, 3, 4, 8, or 12 h (A) and 0, 0.01, 0.1, or 10 μM for 2 h (B) in HUVECs and VEGF-A were amplified by using its specific primers. GAPDH was used as a reference gene.
Figure 5B:
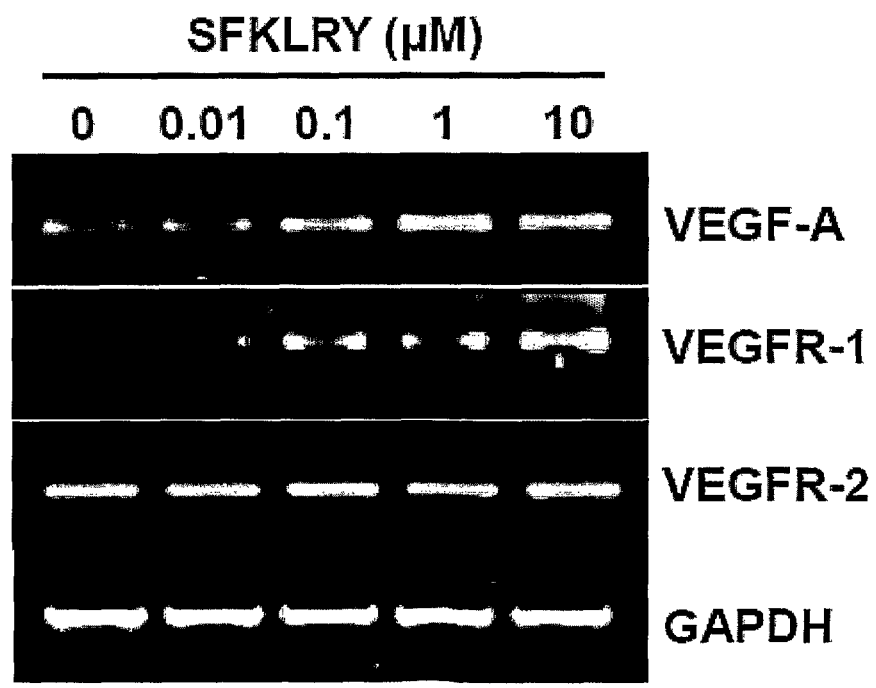

To clarify the possible involvement of the VEGF signaling pathway in the SFKLRY-NH2 (SEQ ID NO: 2)-induced angiogenic process, the expression of angiogenic factors was measured by RT-PCR in HUVECs treated with SFKLRY-NH2 (SEQ ID NO: 2). FIGS. 5A-5B show upregulation of VEGF and VEGFR-1 mRNA by SFKLRY-NH$_2$ (SEQ ID NO: 2). RT-PCR analysis was performed on mRNA isolated from primary cultured HUVECs treated with SFKLRY-NH$_2$ (SEQ ID NO: 2). The data presented are representative of three independent experiments. SFKLRY-NH$_2$ (SEQ ID NO: 2) (10 µM) was treated for 0, 1, 2, 3, 4, 8, or 12 h (A) and 0, 0.01, 0.1, or 10 µM for 2 h (B) in HUVECs and VEGF-A were amplified by using its specific primers. GAPDH was used as a reference gene.

As shown in FIG. 5A, the expression levels of VEGF-A, a strong angiogenic factor increased by 3.77-fold and showed time-dependent manner of induction with maximum expression in 2 h.

The induction of VEGF-A was sustained over 8 and 4 h. On the other hand, SFKLRY-NH$_2$ (SEQ ID NO: 2) stimulation did not affect the expression level bFGF, and FGFR-2 (data not shown). The peptide evoked the inductions of VEGF-A in a dose-dependent manner (FIG. 5B). These data suggest that the enhanced expression of VEGF may be involved in the angiogenic action of SFKLRY-NH2 (SEQ ID NO: 2) in HUVECs.

2.6. SFKLRY-NH$_2$ (SEQ ID NO: 2) Induces Angiogenic Effect Via Up-Regulation of VEGF The inventors showed that possible involvement of VEGF up-regulation in SFKLRY-NH2 (SEQ ID NO: 2)-induced angiogenesis by assessing the increase of the messages for those proteins by RT-PCR analysis (FIGS. 5A & 5B). To further support the possible role of the inductions of VEGF-A in SFKLRY-NH$_2$ (SEQ ID NO: 2)-induced angiogenesis, the effect of VEGF neutralizing antibody on the peptide-induced angiogenesis was examined in tube formation assay.

Figure 6B:
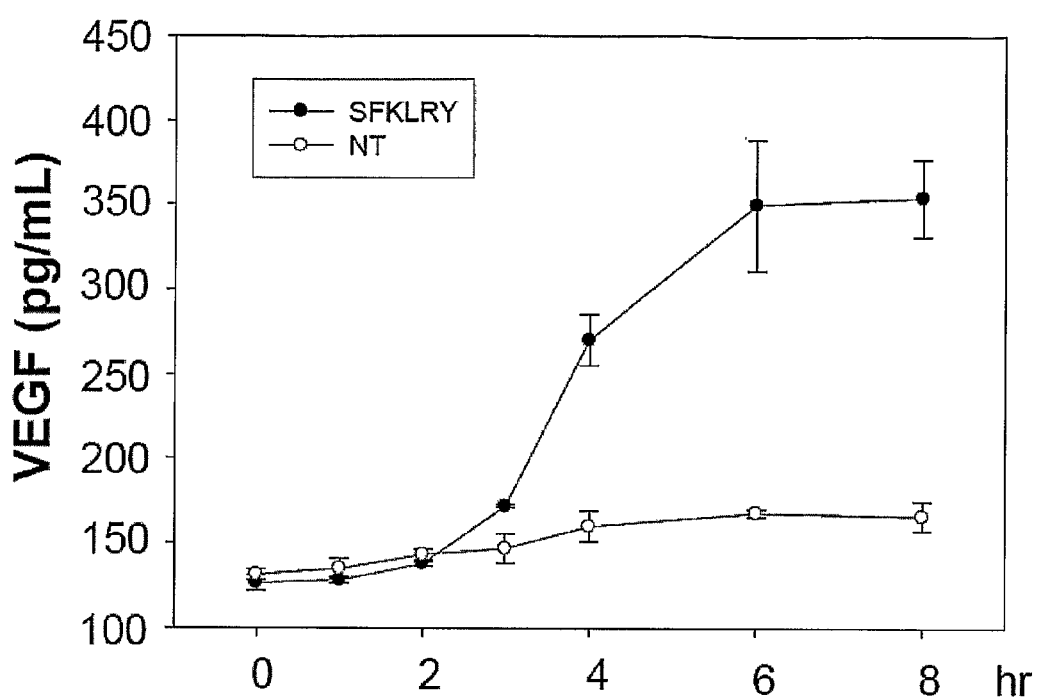

FIGS. 6A-6B show anti-VEGF antibody suppress SFKLRY-NH2 (SEQ ID NO: 2)-induced tube formation in HUVECs. Cells were incubated for 24 h in medium containing SFKLRY-NH$_2$ (SEQ ID NO: 2) (10 µM) or VEGF-A (10 ng/mL) with anti-VEGF-A neutralizing antibody (0.1, 1, or 10 µg/mL). After incubation for 24 h, the tubular-like structures were photographed and the length of tube formation was measured. The data are representative from one of two independent experiments and values are means of the two independent experiments. *P<0.05 compared with vehicle treatment.

SFKLRY-NH2 (SEQ ID NO: 2)-induced HUVECs tube formation (18.2±0.77) showed statistically significant attenuation by co-treatment of VEGF neutralizing antibody with about half inhibition, which is similar level of a control (VEGF+VEGF neutralizing antibody, 12.1±0.63) (FIG. 6A). In addition, a maximal 3.77-fold increase in VEGF-A mRNA expression after SFKLRY-NH2 (SEQ ID NO: 2) stimulation was accompanied by dramatic increases in VEGF-A production by HUVECs, as determined by ELISA (FIG. 6B). These results indicate that induction of VEGF is involved in SFKLRY-NH2 (SEQ ID NO: 2) induced angiogenesis.

To investigate whether SFKLRY-NH2 (SEQ ID NO: 2) might affect angiogenesis by inducing other angiogenic factors, RT-PCR analysis on well-known signaling molecules implicated in angiogenesis was carried out. The present inventors observed the increase of VEGF-A expression as early as 2 h treatment of SFKLRY-NH2 (SEQ ID NO: 2) in HUVECs (FIG. 5), while the level of bFGF, and FGFR-2 expression was not changed (Data not shown). In addition, VEGF-neutralizing antibodies highly suppressed SFKLRY-NH2 (SEQ ID NO: 2)-induced HUVECs tube formation (FIG. 6A). ELISA analysis monitoring VEGF-A proteins secreted into culture media also revealed that SFKLRY-NH2 (SEQ ID NO: 2) stimulation in HUVECs resulted in three-fold increase of VEGF accumulation (FIG. 6B). These results led us to the proposal that the mechanism for SFKLRY-NH2 (SEQ ID NO: 2) induced angiogenic activity is may mediated by inducing VEGF and half-inhibition result with VEGF neutralizing antibody (FIG. 6A) also propose the uncharacterized mediators in angiogenic activity by SFKLRY-NH2 (SEQ ID NO: 2) stimulation.

Recent studies suggest the importance of VEGF induction in clinical setting where transferring of plasmid or adenoviral DNA-encoding VEGF has favorable effect in myocardial infarction and duodenal ulcer healing in animal model (X. Deng, et al., *J Pharmacol Exp Ther* 311 (2004), pp. 982-988; J. Rutanen, et al., *Circulation* 109 (2004), pp. 1029-1035; Y. S. Yoon, et al., *Mol Cell Biochem* 264 (2004), pp. 63-74). Although it should be tested if SFKLRY-NH2 (SEQ ID NO: 2) induces VEGF expression in vivo, the peptide treatment would be more advantageous method than gene delivery, since therapeutic plasmid gene delivery to a target organ is difficult and often temporary. Furthermore, among the known VEGF inducers such as TNF-α, transforming growth factor-β, interleukin-1β, and endothelin (F. Bussolino, et al., *J Pharmacol Exp Ther* 311 (2004), pp. 982-988), SFKLRY-NH2 (SEQ ID NO: 2) is the smallest peptide, which has several advantages over other proteins in the aspect of easier synthesis, lower cost than protein expression and with unnecessary expression system; the present inventors simply get high purity of peptides. Such a potential benefit of SFKLRY-NH2 (SEQ ID NO: 2) on vascular remodeling may suggest a potential use of SFKLRY-NH2 (SEQ ID NO: 2) for human disease evoked by an impaired blood supply, including foot and leg ulcers associated with diabetes or wounds.

Example 3: Promotion of the Healing of Wound in an Animal Model

Wound healing experiments were performed with Sprague-Dawley (6 week-old, male, body weight 140~160 gram), the animals were randomly divided into three groups. Under gerolan anesthesia, the back was shaved and the skin was sterilized with 70% ethanol. Full-thickness wounds were created on the skin of the backs using 8-mm skin biopsy punches. Wound site covered with Tegaderm. The present inventors were administered topically each groups with Control (HBSS), SFKLRY 10 uM and fysrlk 10 uM, once daily, for a period of 14 days. After 14 days, the rats were sacrificed and then the wound tissues were removed. These samples were then separately fixed in 4% formaldehyde, dehydrated through graded alcohol series, cleared in xylene and embedded in paraffin wax. Serial sections of 4 μm were cut, and stained with hematoxylin and eosin (H&E).

Figure 7A:
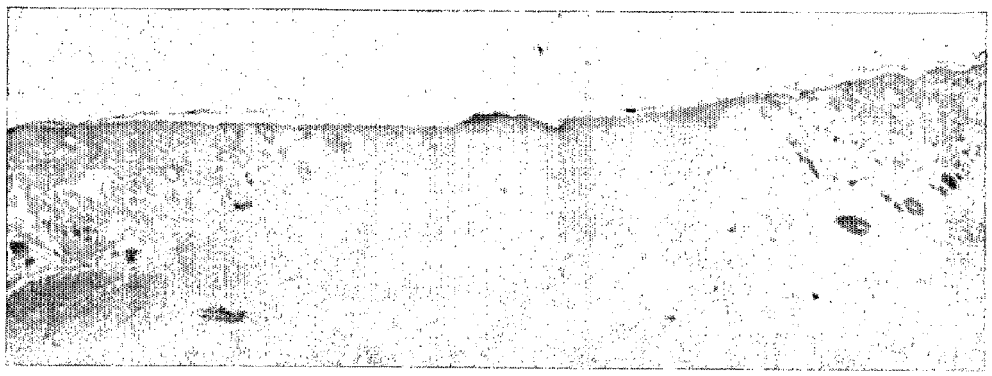
FIGS. 7A-7B show histologies of the healing wound tissues at the day 14. (A) Mock-treated wound shows severe edema and disorganized microarchitectures. (B) The nearly complete restoration of microarchitectures into normal was observed by the treatment with SFKLRY-NH2 (SEQ ID NO: 2) (10 μM).
Figure 7B:
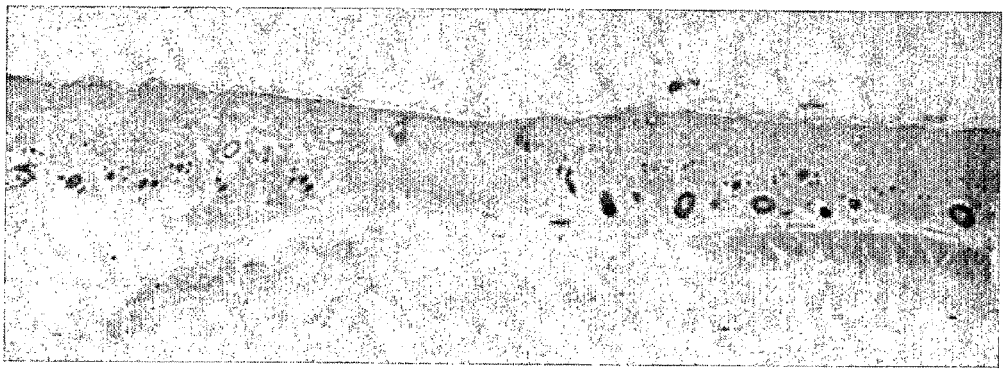

Based on the positive effect of SFKLRY-NH2 (SEQ ID NO: 2) on HUVEC migration in an in vitro wounding migration assay, the effect of SFKLRY-NH2 (SEQ ID NO: 2) on wound was examined in rat model. The histology of biopsied wound tissues at the day 14 are shown in FIGS. 7A & 7B. FIGS. 7A-7B show histologies of the healing wound tissues at the day 14. In FIG. 7A, mock-treated wound shows severe edema and disorganized microarchitectures. In FIG. 7B, the nearly complete restoration of microarchitectures into normal was observed by the treatment with SFKLRY-NH$_2$ (SEQ ID NO: 2) (10 μM).

Compared with control (PBS-treated), the treatment with SFKLRY-NH2 (SEQ ID NO: 2) almost completely restored wound.

Example 4: Induction of Collagen Synthesis

Reminding the possible relationship between blood vessel formation and skin ageing, the potential use of SFKLRY-NH2 (SEQ ID NO: 2) as a constituent of cosmetics against wrinkle was explored. The expression of collagen type I was determined by Western Blot. Fibroblasts from each group were pelleted and extracted in iced cell lysis buffer (Cell Signaling Technologies). Cell lysates were centrifuged at 15 000 g for 15 min at 4° C. and the supernatants from each group were separated by 8% SDS-PAGE and then transferred to nitrocellulose membranes. After incubation in blocking solution (5% nonfat milk), membranes were incubated with primary antibodies (Sigma-Aldrich) overnight at 4° C. Membranes were washed with 1×TBST solution and then incubated with secondary antibody (1:5000 dilution, Amersham Life Sciences) for 2 h. The membranes were detected with the ECL system (Amersham Life Sciences) and relative intensities of protein bands analyzed by Scan-gel-it software.

Figure 8:
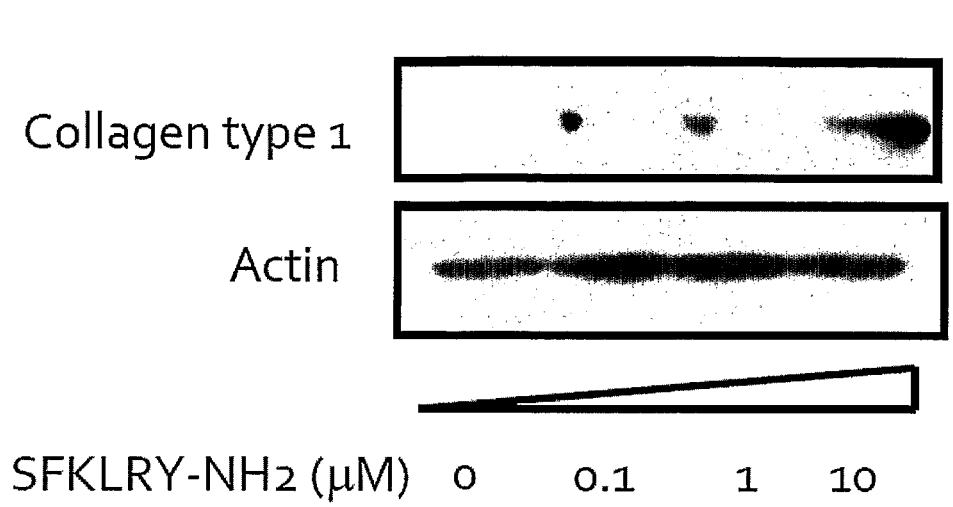
FIG. 8 shows the effect of SFKLRY-NH2 (SEQ ID NO: 2) on collagen type I synthesis. Human fibroblasts were treated with SFKLRY-NH2 (SEQ ID NO: 2) (0.1, 1, 10 μM).

As shown in FIG. 8, SFKLRY-NH2 (SEQ ID NO: 2) significantly enhanced collagen type I expression showing maximal response at the concentration of 10 μM. FIG. 8 shows the effect of SFKLRY-NH2 (SEQ ID NO: 2) on collagen type I synthesis. Human fibroblasts were treated with SFKLRY-NH2 (SEQ ID NO: 2) (0.1, 1, 10 μM). After 24 h, collagen type I expression was determined with the Western Blot. The experiments were repeated three times with reproducible results.

Example 5: Inhibition of Melanin Formation in Melanoma Cells

To explore the possible effect of SFKLRY-NH2 (SEQ ID NO: 2) on melanogenesis, B16 melanoma cells stimulated with α-MSH were cultured in the presence of SFKLRY-NH2 (SEQ ID NO: 2) at the concentration of 1, 10, or 50 μM for 5 d. B16 melanoma cells were treated with a given concentration of SFKLRY-NH2 (SEQ ID NO: 2), followed by α-MSH (10 nM) for 5 d. After treatment, they were detached by a short incubation with trypsin/EDTA. After precipitation, the cell pellets were photographed and solubilized in boiling 2M NaOH for 20 min. Spectrophotometric analysis of the melanin content was performed at 405 nm.

Figure 9A:
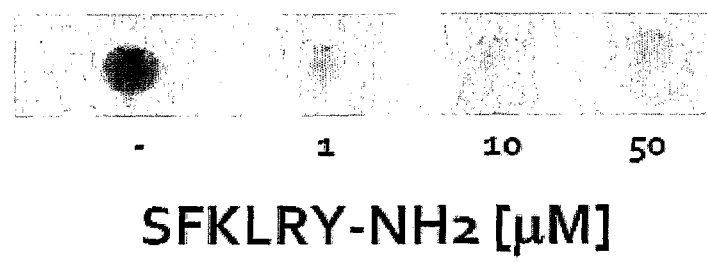
FIGS. 9A-9B show the effect of SFKLRY-NH2 (SEQ ID NO: 2) on melanin content in B16 melanoma cells.
Figure 9B:
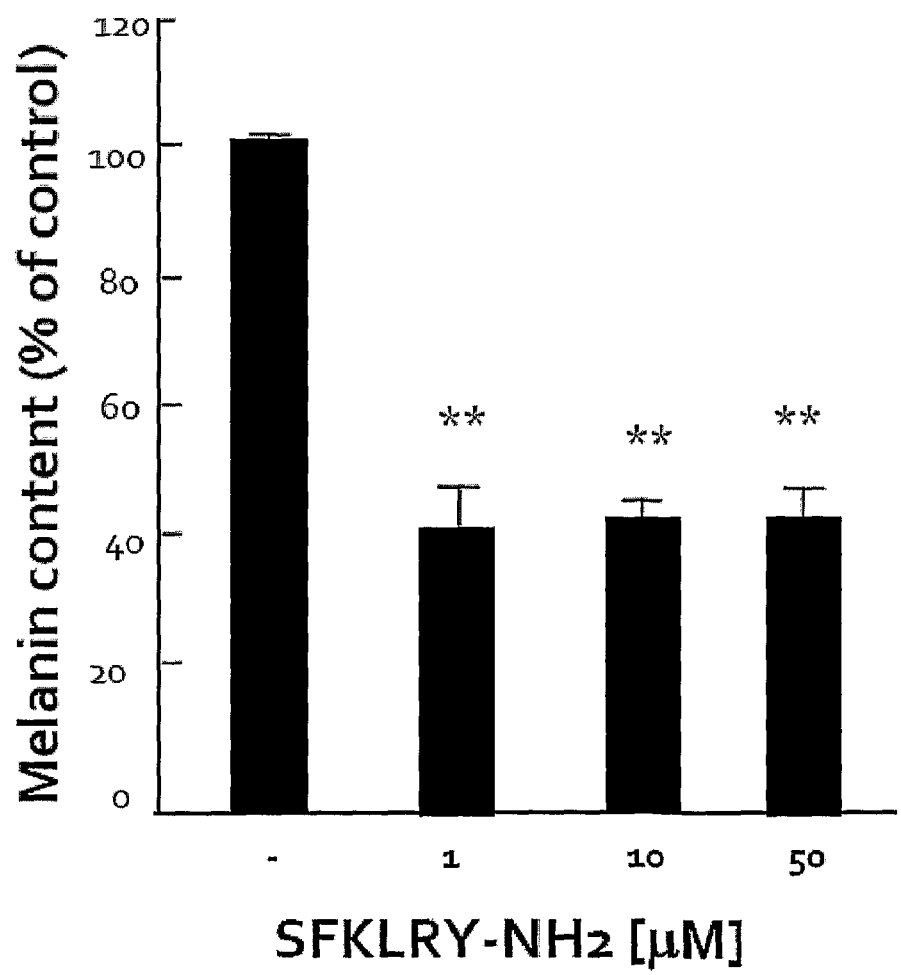

FIGS. 9A-9B show the effect of SFKLRY-NH2 (SEQ ID NO: 2) on melanin content in B16 melanoma cells. In FIG. 9A, B16 melanoma cells were treated with a given concentration of SFKLRY-NH$_2$ (SEQ ID NO: 2), followed by α-MSH (10 nM) for 5 d. After treatment, they were detached by a short incubation with trypsin/EDTA. After precipitation, the cell pellets were photographed in FIG. 9A and solubilized in boiling 2M NaOH for 20 min. Spectrophotometric analysis of the melanin content was performed at 405 nm in FIG. 9B. The experimental results are expressed as percentages of control (α-MSH-treated).

As shown in FIGS. 9A and 9B, the colors of cell pellets are depigmented and treatment with SFKLRY-NH2 (SEQ ID NO: 2) yielded a significant inhibitory effect (around 60% inhibition) on melanin formation displaying saturated response at 1 μM.

All of the references cited herein are incorporated by reference in their entirety. Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A method of promoting angiogenesis in a mammal, comprising administering to a subject in need, an effective amount of a peptide consisting of the amino acid sequence of SFKLRY-NH$_2$ (SEQ ID NO: 2).

2. The method of claim 1, wherein the subject requires angiogenesis for epithelial wound healing.

3. The method of claim 1, wherein the subject requires angiogenesis for inducing collagen synthesis.

4. The method of claim 1, wherein the peptide is administered topically, systematically, orally, or parenterally.

* * * * *